United States Patent
Stadler et al.

(10) Patent No.: US 9,682,244 B2
(45) Date of Patent: Jun. 20, 2017

(54) CARDIAC EVENT SENSING AND PACING AFTER DELIVERY OF AN ELECTRICAL STIMULATION PULSE

(71) Applicant: Medtronic, Inc., Minneapolis, MN (US)

(72) Inventors: Robert W. Stadler, Shoreview, MN (US); Jian Cao, Shorevew, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/519,251

(22) Filed: Oct. 21, 2014

(65) Prior Publication Data

US 2016/0106989 A1    Apr. 21, 2016

(51) Int. Cl.
| | | |
|---|---|---|
| *A61N 1/39* | (2006.01) | |
| *A61N 1/365* | (2006.01) | |
| *A61N 1/362* | (2006.01) | |
| *A61N 1/368* | (2006.01) | |
| *A61N 1/372* | (2006.01) | |

(52) U.S. Cl.
CPC .......... *A61N 1/3962* (2013.01); *A61N 1/365* (2013.01); *A61N 1/368* (2013.01); *A61N 1/3622* (2013.01); *A61N 1/37252* (2013.01)

(58) Field of Classification Search
CPC .......... A61N 1/38; A61N 1/39; A61N 1/3937; A61N 1/3943; A61N 1/3956; A61N 1/3962; A61N 1/3987
See application file for complete search history.

(56) References Cited

U.S. PATENT DOCUMENTS

| | | |
|---|---|---|
| 5,018,522 A | 5/1991 | Mehra |
| 5,331,966 A | 7/1994 | Bennett et al. |
| 5,354,316 A | 10/1994 | Keimel |
| 5,411,524 A * | 5/1995 | Rahul ............ A61N 1/39 607/9 |
| 5,447,519 A | 9/1995 | Peterson |
| 5,545,186 A | 8/1996 | Olson et al. |
| 5,645,569 A | 7/1997 | Ayers |
| 5,658,317 A | 8/1997 | Haefner et al. |
| 5,676,687 A | 10/1997 | Ayers |
| 6,081,748 A | 6/2000 | Struble et al. |
| 6,141,583 A | 10/2000 | Pape et al. |
| 6,157,859 A | 12/2000 | Alt |
| 6,330,477 B1 | 12/2001 | Casavant |

(Continued)

OTHER PUBLICATIONS (PCT/US2015/054124) PCT Notification of Transmittal of the International Search Report and the Written Opinion of the International Searching Authority, Mailed Dec. 11, 2015, 13 pages.

*Primary Examiner* — Eric D. Bertram
(74) *Attorney, Agent, or Firm* — Michael J. Ostrom

(57) ABSTRACT

A medical device is configured to deliver a shock to a patient's heart via electrodes coupled to the medical device and set an escape interval timer to start running an escape interval after delivering the electrical shock. A sensing module of the medical device is configured to sense a cardiac event in response to a cardiac electrical signal received by the medical device crossing a sensing threshold. The medical device determines if the cardiac event meets reset criteria and allows the escape interval timer to continue running the escape interval if the cardiac event does not meet the reset criteria.

31 Claims, 8 Drawing Sheets

(56) References Cited

U.S. PATENT DOCUMENTS

| | | |
|---|---|---|
| 6,377,851 B1 * | 4/2002 | Shieh et al. ........... A61N 1/362 607/9 |
| 6,393,316 B1 | 5/2002 | Gillberg et al. |
| 6,496,730 B1 | 12/2002 | Kleckner et al. |
| 6,745,068 B2 | 6/2004 | Koyrakh et al. |
| 7,031,771 B2 | 4/2006 | Brown et al. |
| 7,353,062 B2 | 4/2008 | Kim et al. |
| 7,392,081 B2 | 6/2008 | Wagner et al. |
| 7,496,408 B2 | 2/2009 | Ghanem et al. |
| 7,496,409 B2 | 2/2009 | Greenhut et al. |
| 7,570,997 B2 | 8/2009 | Lovett et al. |
| 7,593,771 B2 | 9/2009 | Yonce et al. |
| 7,610,087 B2 | 10/2009 | Öhman et al. |
| 7,991,470 B2 | 8/2011 | Kim et al. |
| 8,160,684 B2 | 4/2012 | Ghanem et al. |
| 8,214,038 B2 | 7/2012 | Kim et al. |
| 8,301,233 B2 | 10/2012 | Zhang et al. |
| 8,332,022 B2 | 12/2012 | Brown et al. |
| 8,437,842 B2 | 5/2013 | Zhang et al. |
| 8,483,841 B2 | 7/2013 | Sanghera et al. |
| 2004/0088019 A1 | 5/2004 | Rueter et al. |
| 2005/0245976 A1 * | 11/2005 | Wang ..................... A61N 1/362 607/9 |
| 2006/0064027 A1 | 3/2006 | Borowitz et al. |
| 2006/0253009 A1 | 11/2006 | Stubbs et al. |
| 2007/0038253 A1 | 2/2007 | Kim et al. |
| 2007/0055314 A1 | 3/2007 | Bardy et al. |
| 2015/0367135 A1 * | 12/2015 | Whittington et al. ................... A61N 1/3962 607/9 |

* cited by examiner

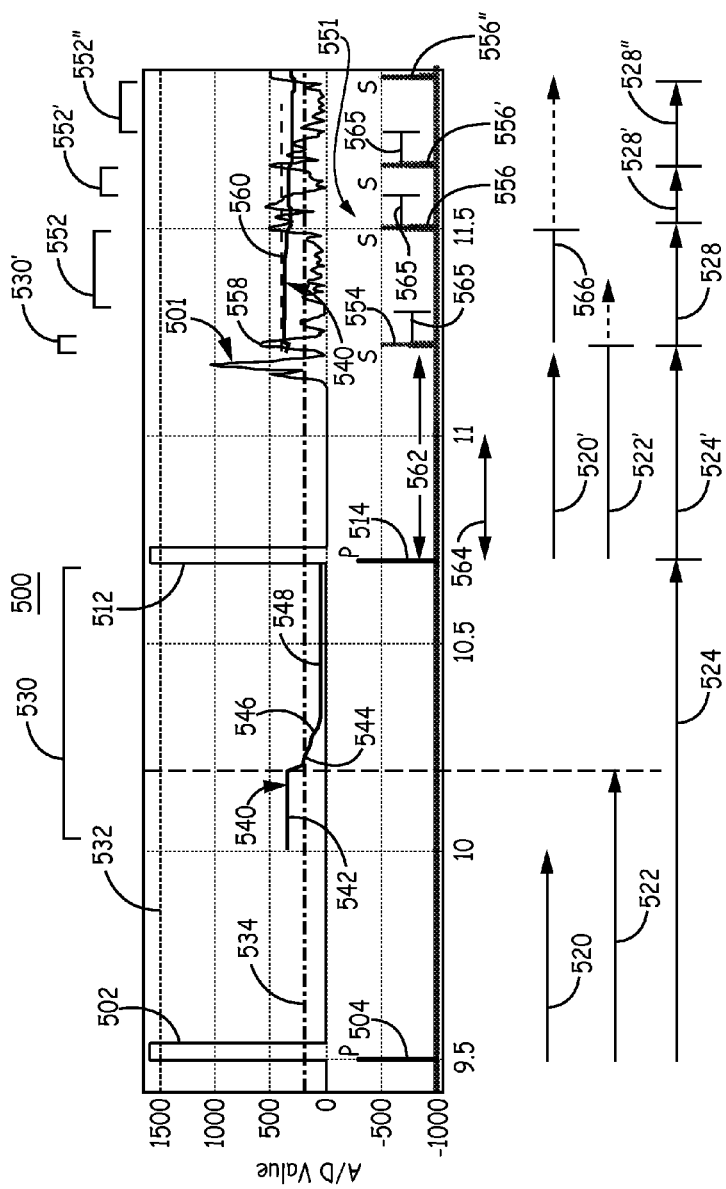
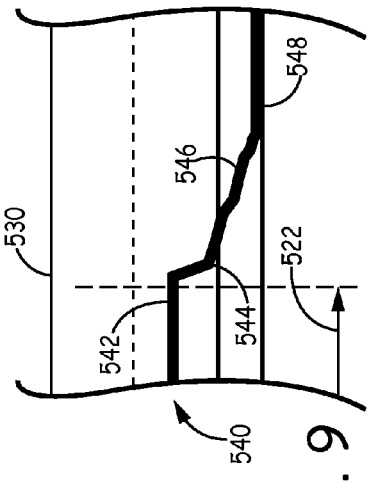
FIG. 8
FIG. 9

CARDIAC EVENT SENSING AND PACING AFTER DELIVERY OF AN ELECTRICAL STIMULATION PULSE

TECHNICAL FIELD

The disclosure relates generally to implantable medical devices and, in particular, to a method and apparatus for sensing cardiac electrical signals and controlling pacing pulses delivered after an electrical stimulation pulse is delivered to a patient's heart.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, e.g., implanted in the heart through one or more veins. Other leads may be non-transvenous leads implanted outside the heart, e.g., implanted epicardially, pericardially, or subcutaneously. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal cardiac rhythms. Upon detection of an abnormal rhythm, the device may deliver an appropriate electrical stimulation signal or signals to restore or maintain a more normal rhythm. For example, an IMD may deliver pacing pulses to the heart upon detecting asystole, tachycardia or bradycardia, and deliver cardioversion or defibrillation shocks to the heart upon detecting tachycardia or fibrillation.

SUMMARY

In general, the disclosure is directed to techniques for sensing cardiac signals after delivery of an electrical stimulation pulse, such as a cardioversion (CV) or defibrillation (DF) shock, to a patient's heart and controlling post-stimulation pacing pulses. An implantable cardioverter defibrillator (ICD) operating in accordance with the techniques of this disclosure senses cardiac electrical signal events and controls post-shock pacing pulse delivery during a post-shock pacing period. The ICD allows an escape interval timer to continue running an escape interval during the post-shock pacing period if a cardiac event sensed during the pacing escape interval does not meet escape interval reset criteria.

In one example, the disclosure provides a method comprising delivering an electrical shock to a heart of a patient, setting an escape interval timer to start running an escape interval after delivering the electrical shock, sensing a cardiac event in response to a cardiac electrical signal received by the medical device crossing a sensing threshold during the escape interval, determining if the cardiac event meets reset criteria; allowing the escape interval timer to continue running the escape interval if the cardiac event does not meet the reset criteria, and resetting the escape interval timer in response to the cardiac event meeting the reset criteria.

In another example, the disclosure provides a medical device comprising a therapy delivery module configured to deliver an electrical shock to a patient's heart via electrodes coupled to the medical device, a sensing module configured to receive a cardiac electrical signal, and a control module coupled to the sensing module and the therapy delivery module. The control module is configured to set an escape interval timer to start running an escape interval after the therapy delivery module delivers the electrical shock, determine if a sensed cardiac event meets reset criteria, allow the escape interval timer to continue running the escape interval if the cardiac event does not meet the reset criteria and reset the escape interval timer in response to the cardiac event meeting the reset criteria.

In another example, the disclosure provides a non-transitory, computer-readable storage medium comprising instructions that, when executed by a control module in a medical device, cause the medical device to deliver a shock to a patient's heart via electrodes coupled to the medical device, set an escape interval timer to start running an escape interval after delivering the electrical shock, sense a cardiac event in response to a cardiac electrical signal received by the medical device crossing a sensing threshold, determine if the cardiac event meets reset criteria, allow the escape interval timer to continue running the escape interval if the cardiac event does not meet the reset criteria and reset the escape interval timer in response to the cardiac event meeting the reset criteria.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 8 is a timing diagram illustrating a cardiac electrical signal, an automatically adjusted R-wave sensing threshold, and R-wave sense event signals produced by an ICD post-shock according to one example.

FIG. 9 is an enlarged view of a portion of a post-pace decay sequence shown in FIG. 8.

DETAILED DESCRIPTION

Figure 1:
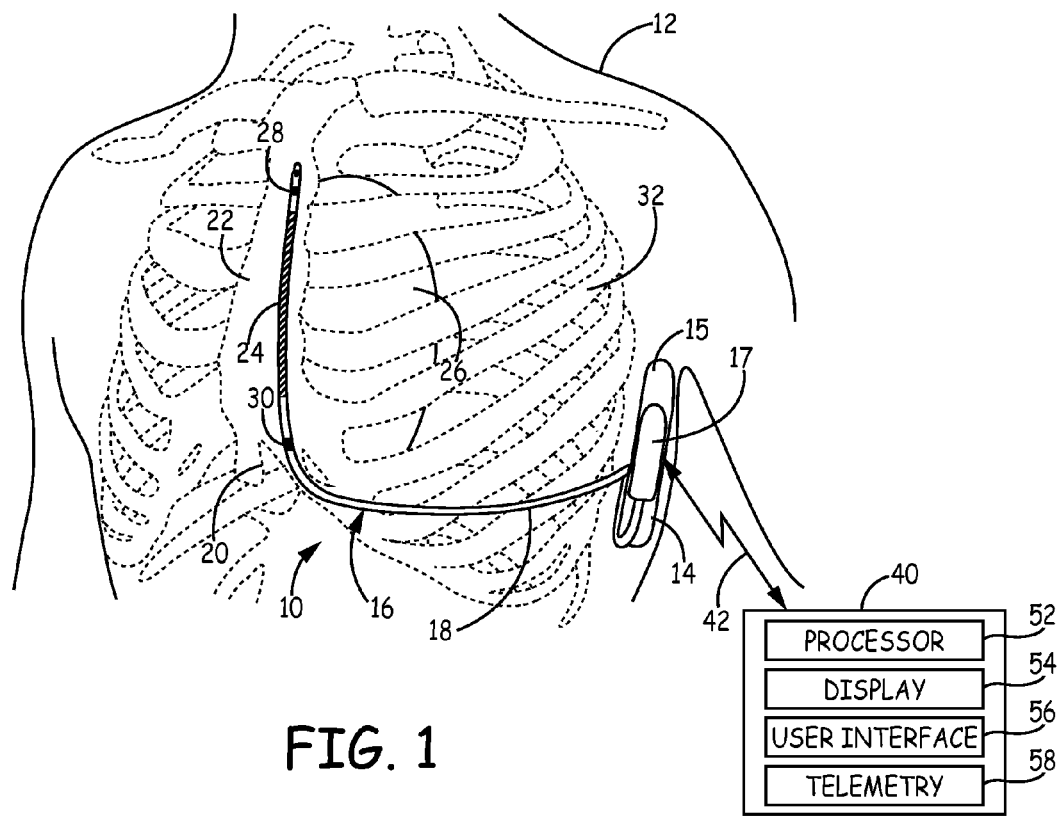
FIG. 1 is a conceptual diagram of a patient implanted with an example IMD system that includes an ICD coupled to a subcutaneous defibrillation and sensing lead.

In general, this disclosure describes techniques for sensing cardiac events and determining a need for post-shock pacing of a patient's heart. When a shockable rhythm is detected, a CV/DF shock is delivered by an ICD. Techniques disclosed herein include methods performed by an ICD for controlling post-shock pacing escape intervals and automatically adjusting a cardiac event sensing threshold following a post-shock pacing pulse.

Shockable arrhythmias refer to abnormal heart rhythms for which a shock therapy is delivered to one or both of the ventricles. Shockable arrhythmias may include ventricular tachycardia (VT) and ventricular fibrillation (VF). Shockable arrhythmias generally pose an immediate danger to the patient and therapy is needed in order to ensure the safety of the patient. Non-shockable arrhythmias, on the other hand, refer to normal or abnormal intrinsic heart rhythms that typically do not require a shock therapy to be delivered to either of the ventricles. Non-shockable cardiac rhythms may include supra-ventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-shockable arrhythmias do not generally pose an immediate danger to the patient. As such, non-shockable arrhythmias may go untreated, i.e., no shock therapy is delivered to the heart. In other instances, non-shockable arrhythmias may be treated using an electrical stimulation therapy, but the electrical stimulation therapy may be a low-voltage pacing therapy or is not delivered to the ventricles of the patient.

A shock therapy generally includes at least one a high-voltage shock pulse, which may be in the range of at least 10 Joules and up to 35 Joules for transvenous lead systems carrying intracardiac cardioversion/defibrillation electrodes and in the range of at least 65 Joules and up to 80 Joules for subcutaneous lead systems carrying extracardiac cardioversion/defibrillation electrodes. After delivering a shock therapy, accurate determination of whether the shockable rhythm has been terminated is needed so that, if the shockable arrhythmia is not terminated, another shock can be promptly delivered, typically with a higher or maximum shock energy. In some cases, even if the shock successfully terminates the shockable rhythm, post-shock pacing is required to treat asystole or low-amplitude R-waves that may occur post-shock while the heart recovers from the CV/DF shock.

Cardiac electrical signals, such as a subcutaneous electrocardiogram (ECG) or an intracardiac electrogram (EGM), are received by an ICD via implanted electrodes coupled to the ICD. The cardiac electrical signals are analyzed by the ICD to initially detect a shockable heart rhythm, redetect the shockable rhythm post-shock, and/or determine a need for post-shock pacing. The cardiac electrical signal includes cardiac event signals attendant to the depolarization (e.g., R-waves) and the repolarization (e.g., T-waves) of the ventricles.

An ICD according to the present disclosure includes a sensing module configured to sense cardiac event signals, such as R-waves, subsequent to delivering a post-shock pacing pulse using an automatically adjusted post-pace cardiac event sensing threshold during a post-shock sensing period that enables the ICD to reliably sense cardiac events after post-shock pacing pulses. The automatic adjustment of the post-pace cardiac event sensing threshold, e.g., an R-wave sensing threshold, used during the post-shock sensing period is modified compared to an auto-adjusting sensing threshold used pre-shock in order to promote proper detection of low amplitude post-shock fibrillation waves, low amplitude R-waves or asystole post-shock. The ICD includes a therapy delivery module for generating post-shock pacing pulses upon expiration of an escape interval timer that is controlled based on characteristics of sensed cardiac events.

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal end that includes one or more electrodes. Defibrillation lead 16 is illustrated in FIG. 1 as being implanted subcutaneously, e.g., in tissue and/or muscle between the skin and the ribcage 32 and/or sternum 22. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. Although illustrated as being offset laterally from and extending substantially parallel to sternum 22 in the example of FIG. 1, defibrillation lead 16 may be implanted over sternum 22, offset from sternum 22, but not parallel to sternum 22 (e.g., angled laterally from sternum 22 at either the proximal or distal end).

Figure 2:
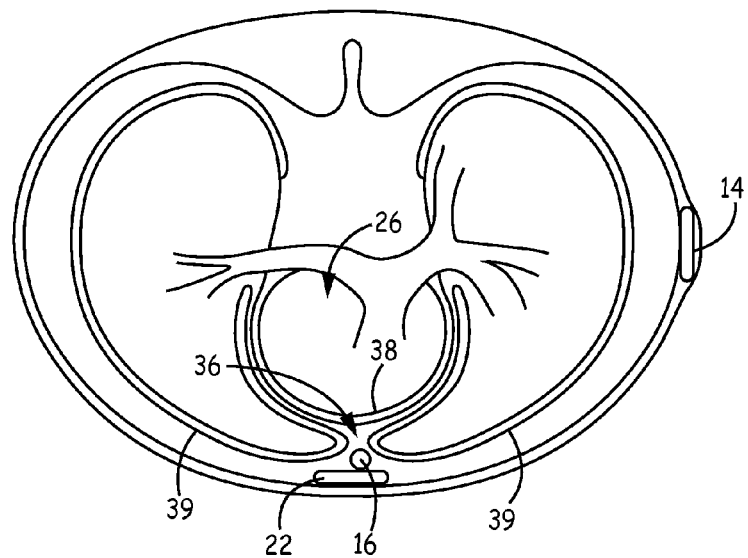
FIG. 2 is a transverse view of the patient in FIG. 1 depicting the defibrillation and sensing lead implanted in an alternate location.

In other instances, lead 16 may be implanted at other extravascular locations. As shown in a transverse view of patient 12 in FIG. 2, lead 16 may be implanted at least partially in a substernal location, e.g., between the ribcage and/or sternum 22 and heart 26. In one such configuration, a proximal portion of lead 16 extends subcutaneously from ICD 14 toward sternum 22 (not seen in the transverse view of FIG. 2) and a distal portion of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26 and not above sternum 22 or ribcage.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and distal electrode coil 24 and distal sensing electrode 28.

Referring again to FIG. 1, lead 16 includes an elongated lead body 18 carrying electrodes 24, 28 and 30 located along the distal portion of the length of the lead body 18. Lead body 18 insulates one or more elongated electrical conductors (not illustrated) that extend from a respective electrode 24, 28 and 30 through the lead body 18 to a proximal connector (not shown) that is coupled to ICD 14. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy module or a sensing module, via connections in an ICD connector assembly 17 that includes a connector bore for receiving the proximal connector of lead 16 and associated electrical feedthroughs crossing ICD housing 15. The electrical conductors transmit therapy from a therapy module within ICD 14 to one or more of electrodes 24, 28, and 30, and transmit cardiac electrical signals from one or more of electrodes 24, 28, and 30 to the sensing module within ICD 14.

Defibrillation lead 16 is shown in FIG. 1 to include a defibrillation electrode 24, which may be an elongated coil electrode, along the distal portion of defibrillation lead 16. Defibrillation electrode 24 is located on lead 16 such that when ICD system 10 is implanted a therapy vector between defibrillation electrode 24 and a housing or can electrode 15 of ICD 14 is substantially through or across the ventricle(s) of heart 26.

Defibrillation lead 16 also includes one or more sensing electrodes 28 and 30, located toward the distal portion of defibrillation lead 16. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. ICD system 10 may sense electrical activity of heart 26 via one or more sensing vectors that include combinations of electrodes 28 and 30 and the housing or can electrode 15 of ICD 14. For example, ICD 14 may receive a subcutaneous ECG signal across a sensing vector between electrodes 28 and 30, a sensing vector between electrode 28 and the conductive housing or can electrode 15, a sensing vector between electrode 30 and the conductive housing or can electrode 15, or any combination of electrodes 28, 30 and the housing or can electrode 15. In some instances, ICD 14 may even sense cardiac electrical signals using a sensing vector that includes defibrillation electrode 24.

ICD 14 analyzes the electrical signals received from one or more of the sensing vectors described above to detect and treat shockable tachyarrhythmias, such as VT or VF. ICD 14 may deliver one or more cardioversion or defibrillation shocks via defibrillation electrode 24 in response to detecting VT or VF. ICD 14 may also provide pacing therapy, such as anti-tachycardia pacing (ATP) and/or post-shock pacing after a cardioversion or defibrillation shock when pacing capabilities are available. As described herein, ICD 14 analyzes the cardiac electrical signals received from one or more of the sensing vectors after delivery of a CV/DF shock to determine if post-shock pacing is required or if a repeated CV/DF shock is required. If post-shock pacing is required, ICD 14 controls the pace timing and post-pace sensing in accordance with the techniques described herein.

ICD 14 includes a housing 15, also referred to herein as housing electrode or can electrode 15, which forms a hermetic seal that protects internal electronic components of ICD 14. The housing 15 may be formed of a conductive material, such as titanium, titanium alloy, or other conductive material to serve as an electrode. Housing 15 may function as a "can electrode" since the conductive housing or a portion thereof may be coupled to internal circuitry to be used as an indifferent or ground electrode during sensing or cardioversion/defibrillation shock delivery.

ICD 14 also includes connector assembly 17 (also referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this case, defibrillation lead 16 may extend subcutaneously from the device toward the manubrium of the sternum 22 and bend or turn and extend subcutaneously or substernally inferiorly from the manubrium of the sternum, substantially parallel with the sternum.

The techniques disclosed herein may be implemented in numerous ICD and electrode configurations that include one or more housing-based electrodes and/or one or more lead-based electrodes for enabling sensing of a cardiac electrical signal developed across one or more sensing vectors and for delivering electrical stimulation therapies to heart 26 including at least a shock therapy. The IMD system 10 is an extravascular IMD system because lead 16 is positioned in an extravascular location outside the blood vessels, heart 26 and pericardium 38. It is understood that while ICD 14 and lead 16 may be positioned between the skin and a muscle layer of the patient 12, ICD 14 and any associated leads could be positioned in any extravascular location of the patient, such as below a muscle layer or even within the thoracic cavity.

An external device 40 is shown in telemetric communication with ICD 14 by a communication link 42. External device may include a processor 52, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters and ECG signals retrieved from ICD 14. User interface 56 which may include a mouse, touch screen, key pad or the like to enable a user to interact with external device 40 to initiate a telemetry session with ICD 14 for retrieving data from and/or transmitting data to ICD 14. Telemetry unit 58 is configured for bidirectional communication with a telemetry module included in ICD 14 and is configured to operate in conjunction with processor 52 for sending and receiving data relating to ICD functions via communication link 42.

Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD 14 functions. For example, external device 40 may be used to program cardiac event sensing parameters such as parameters used to control a cardiac event sensing threshold according to a post-pace decay sequence during a post-shock sensing period as described below. External device 40 may be used to program ICD therapy control parameters, including post-shock pacing control parameters and shock therapy control parameters. External device 40 may also be used to program ICD tachyarrhythmia detection parameters and criteria relating to the rate, intervals, and/or morphology of ECG cardiac event signals External device 40 may alternatively be embodied as a home monitor or hand held device.

Examples of other IMD systems in which the techniques disclosed herein could be implemented for post-shock sensing of cardiac events and detection of a shockable rhythm after a shock therapy are generally disclosed in U.S. Pat. No. 8,332,022 (Brown et al.) and U.S. Pat. No. 5,447,519 (Peterson), and U.S. Pat. No. 7,496,409 (Greenhut, et al.), all of which patents are incorporated herein by reference in their entirety.

Figure 3:
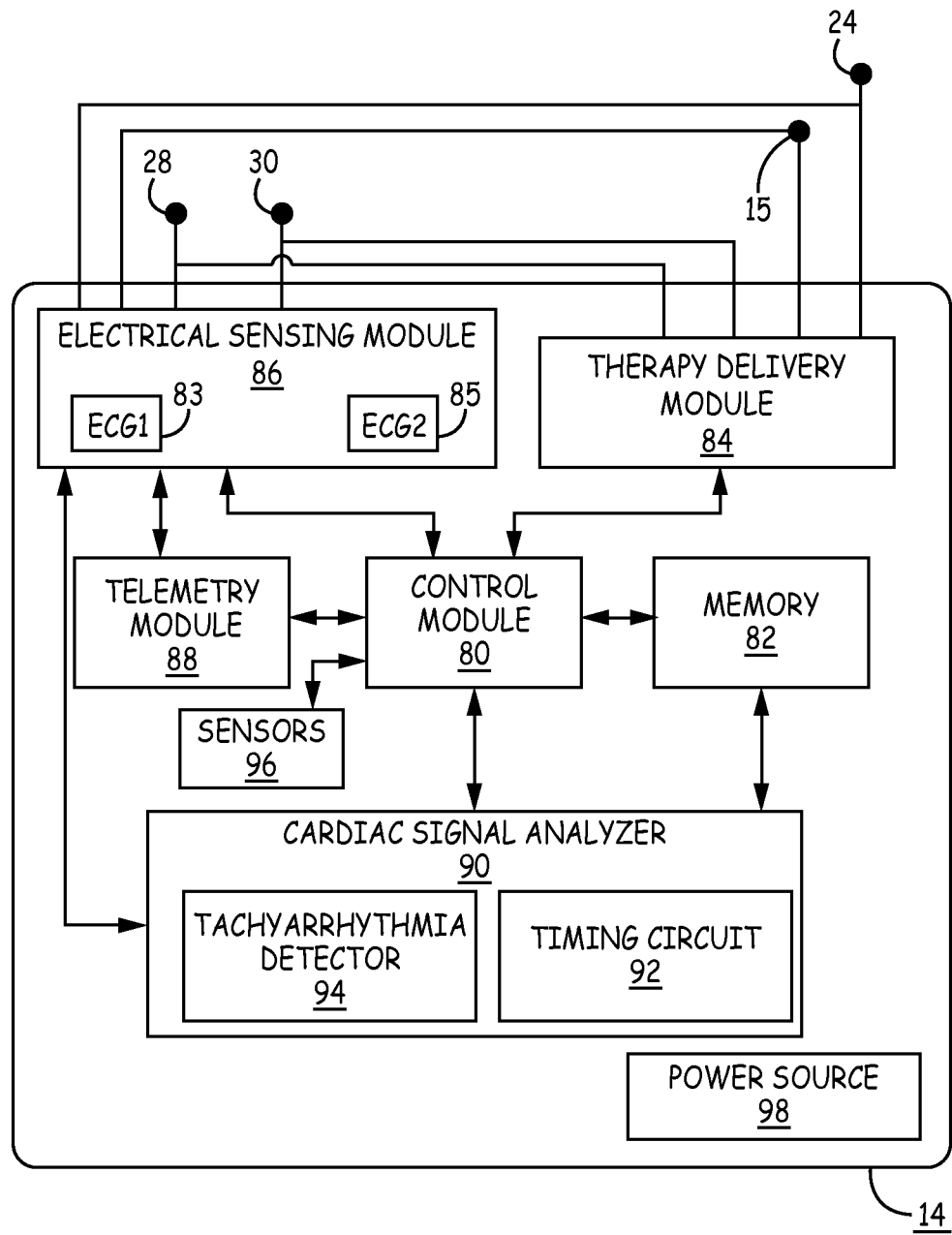
FIG. 3 is a schematic diagram of an ICD according to one embodiment.

FIG. 3 is a schematic diagram of ICD 14 according to one example. The electronic circuitry enclosed within housing 15 includes software, firmware and hardware that cooperatively monitor one or more ECG signals, determine when a CV/DF shock or pacing therapy is necessary, and deliver prescribed CV/DF and pacing therapies. In some examples, ICD 14 may be coupled to a lead, such as lead 16, carrying electrodes, such as electrodes 24, 28 and 30, positioned in operative relation to the patient's heart for delivering cardiac pacing pulses, including post-shock pacing, in addition to shock therapies and may therefore include the capability to deliver low voltage pacing pulses as well as the high voltage shock pulses.

ICD 14 includes control module 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 may be implemented in control module 80 executing instructions stored in memory 82.

As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the device. Providing software, hardware, and/or firmware to accomplish the described functionality in the context of any modern ICD, given the disclosure herein, is within the abilities of one of skill in the art.

Control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 (shown in FIG. 1) and housing electrode 15, which may serve as a common or ground electrode.

Electrical sensing module 86 is selectively coupled to electrodes 28, 30 and housing electrode 15 in order to monitor electrical activity of the patient's heart. Electrical sensing module 86 may additionally be selectively coupled to electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing electrode 15. Sensing module 86 is shown to include two sensing channels 83 and 85 in the example of FIG. 3. Each sensing channel 83 and 85 may be configured to amplify and filter the ECG signal received from selected electrodes coupled to the respective sensing channel to improve the signal quality for sensing cardiac events, e.g., R-waves.

In one example, a first sensing channel 83 (ECG1) may be selectably configured to sense an ECG signal between sensing electrode 28 and ICD housing electrode 15 and a second sensing channel 85 (ECG2) may be selectably configured to sense an ECG signal between sensing electrode 30 and ICD housing electrode 15. In another example, one sensing channel 83 or 85 may receive an ECG signal using electrodes 28 and 30 and the other sensing channel 83 or 85 may receive an ECG signal using one of electrodes 28 and 30 paired with the housing electrode 15.

Each sensing channel 83 and 85 includes cardiac event detection circuitry for sensing cardiac event signals from the received ECG signal developed across the selected electrodes 24, 28, 30 or 15. Cardiac event sensing thresholds used by each sensing channel 83 and 85 are automatically adjusted according to sensing control parameters, which may be stored in memory 82. Control of the automatically-adjusted cardiac event sensing threshold for each sensing channel 83 and 85 may be implemented in control module 80, sensing module 86 or a combination of both. A given sensing channel 83 and 85 senses a cardiac event when the respective received ECG signal crosses auto-adjusting cardiac event sensing threshold outside a blanking interval.

As described below, sensing module 86 may control the auto-adjusting cardiac event sensing threshold according to a post-pace decay sequence and a post-sense decay sequence during a post-shock sensing period following delivery of a CV or DF shock. Alternatively, the sensing module 86 may control the auto-adjusting cardiac event sensing threshold according to a post-pace decay sequence and a post-sense decay sequence in other instances in which rapid recovery of sensing is needed following a pacing pulse or sensing is needed to discriminate fine VF (which needs to be treated by delivering a shock) from asystole (which needs to be treated by pacing).

The post-pace decay sequence includes at least an initial sensing threshold amplitude and a post-pace drop time interval and may include at least one post-pace decay rate. The post-pace decay sequence is used to adjust the R-wave sensing thresholds used by the sensing channels 83 and 85 until the first R-wave sense signal is produced by the respective sensing channel 83 or 85 after a post-shock pacing pulse is delivered.

After the first, post-pace R-wave sense signal is produced by a given sensing channel 83 or 85, the sensing module 86 controls the auto-adjusting R-wave sensing threshold for that sensing channel according to a post-sense decay sequence that is used for sensing R-waves until the next post-shock pacing pulse is delivered. The post-sense decay sequence includes at least an initial sensing threshold amplitude and post-sensed drop time interval and may include at least one decay rate.

The post-pace decay sequence is controlled by a first set of sensing control parameters, and the post-sense decay sequence is controlled by a second set of sensing control parameters different than the first set of sensing control parameters so that the post-pace decay sequence is different than the post-sense decay sequence. For example, at least the initial threshold amplitude is set according to different control parameters for the post-pace and post-sense decay sequences. The cardiac event sensing thresholds for each sensing channel 83 and 85 may be controlled independently using the same or different post-pace decay sequence control parameters.

Each time the filtered and rectified cardiac electrical signal crosses the auto-adjusting sensing threshold for a given channel 83 or 85 outside a blanking interval, a cardiac event sense signal, also referred to herein as a "sense event signal" such as an "R-wave sense event signal," is produced and passed to control module 80 and/or cardiac signal analyzer 90. For example, R-wave sense event signals may be passed to tachyarrhythmia detector 94 and timing circuit 92 of cardiac signal analyzer 90 when a filtered and rectified cardiac electrical signal crosses the auto-adjusting R-wave sensing threshold for a given channel 83 or 85.

Sense event signals produced by sensing channel 83 or 85 during an escape interval set by timing circuit 92 cause cardiac signal analyzer 90 to determine if escape interval reset criteria are met as further described below. Not all sense event signals will cause the escape interval timer to be reset in some examples. Only sense event signals corresponding to sensed events that meet escape interval reset criteria will cause the escape interval timer to be reset. In other words, the reset criteria include requirements in addition to the requirement that the cardiac signal crosses the cardiac event sensing threshold outside a blanking interval. In some examples, a sensing refractory period may be applied following a sensed event. An event sensed during a refractory period may or may not meet reset criteria depending on the particular application.

If escape interval reset criteria are met by a sensed event during the escape interval, the escape interval timer is reset. If reset criteria are not met during the escape interval, the escape interval expires and a post-shock pacing pulse is delivered. If two (or more) sensing channels 83 and 85 are included in sensing module 86, a sensed cardiac event on either channel 83 or 85 that meets the escape interval reset criteria may cause the timing circuit 92 to reset the escape interval timer. In other words, reset criteria met by a cardiac event on a single channel may cause the escape interval to be reset without requiring a cardiac event to meet the reset criteria on the other channel(s).

During the post-shock pacing period, as pacing pulses are delivered as needed, ECG signal analysis may be performed by cardiac signal analyzer 90 to redetect a shockable rhythm using sense event signals and/or a digitized cardiac signal received from sensing module 86. Redetection of a shockable rhythm is performed using an implemented redetection algorithm. The techniques disclosed herein for sensing cardiac events and delivering pacing pulses during a post-shock pacing period are not limited to a particular redetection algorithm.

Sensing module 86 may include an analog-to-digital converter for providing a digital ECG signal from one or all sensing channels 83 and 85 to control module 80 and/or cardiac signal analyzer 90. For example two ECG signals as described above may each be converted to a multi-bit digital signal by sensing module 86 and provided to tachyarrhythmia detector 94 for performing ECG morphology analysis. Analysis of the ECG signal morphology may be used to re-detect a shockable rhythm post-shock.

Cardiac signal analyzer 90 includes a tachyarrhythmia detector 94 for detecting and discriminating shockable and non-shockable rhythms. Cardiac signal analyzer 90 may further include a timing circuit 92 that includes various timers and/or counters for measuring time intervals, such as RR intervals, setting time segments or windows such as morphology template windows, morphology analysis windows relative to R-wave sense signals, post-shock cardiac signal analysis time segments, also referred to herein as "signal analysis segments", or for performing other timing related functions of cardiac signal analyzer 90 including synchronizing cardioversion shocks or other therapies delivered by therapy delivery module 84 with sensed cardiac events. Timing circuit 92 may include an escape interval timer used to control post-shock pacing pulse delivery by therapy module 82 during a post-shock sensing period as described herein.

The timing of R-wave sense signals received from sensing module 86 is used by timing circuit 92 to determine RR intervals between sense event signals. Tachyarrhythmia detector 94 may count RR intervals measured by timing circuit 92 that fall into different rate detection zones for determining a ventricular rate or performing other rate- or interval-based assessment for detecting and discriminating shockable and non-shockable rhythms.

Examples of algorithms that may be performed by ICD 14 for detecting, discriminating and treating shockable rhythms, which may be adapted to include techniques described herein for sensing post-shock cardiac signals and delivering post-shock pacing as needed, are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), U.S. Pat. No. 8,301,233 (Zhang et al.), and U.S. Pat. No. 8,437,842 (Zhang, et al.), all of which patents are incorporated herein by reference in their entirety. The detection algorithms are highly sensitive and specific for the presence or absence of life threatening, shockable VT and VF.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

Therapy delivery module 84 includes a high voltage (HV) therapy delivery module including one or more HV output capacitors for delivering HV CV/DF shock pulses. The high voltage therapy delivery module may be configured for generating and delivering cardiac pacing pulses, e.g., transthoracic pacing pulses delivered using electrodes carried by lead 16 for treating post-shock asystole, and/or tachyarrhythmia induction pulses delivered to induce VT or VF during ICD testing. In other instances, therapy delivery module may include a low voltage therapy delivery module for delivering cardiac pacing pulses, including post-shock pacing pulses. When a malignant tachycardia is detected the HV capacitors are charged to a pre-programmed voltage level by a HV charging circuit. In some examples, a decision to start charging HV output capacitors may be made by control module 80 in response to a cardiac cycle length estimate made by cardiac signal analyzer 90. If additional signal analysis performed by cardiac signal analyzer 90 confirms re-detection of a shockable rhythm, HV output capacitor charging continues, and another shock is delivered.

Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing electrode 15.

Timing circuit 92 may be used to control R-wave synchronized CV shock pulses delivered by therapy delivery module 84.

Therapy delivery module 84 may be configured to deliver (via either the HV therapy delivery module or the low voltage therapy delivery module) relatively high amplitude pacing pulses, e.g., up to 40 volts or higher or up to 200 milliamps or higher, to provide subcutaneously delivered transthoracic pacing pulses. Therapy delivery module 84 may programmed to deliver pulses having a pulse width between 5 ms and 10 ms. For example, 200 mA post-shock pacing pulses may be delivered, having an amplitude between 15 and 40 Volts and a pulse width between 8 and 10 ms for treating post-shock asystole. In some examples, the therapy delivery module 84 may be configured to deliver transthoracic pacing pulses according to aspects disclosed in U.S. Pat. No. 5,018,522 (Mehra), which employs a ramped pacing pulse to reduce pain associated with transthoracic pacing. Pacing pulse amplitudes, shapes and durations may be selected to provide transthoracic post-shock pacing pulses that effectively capture the heart to treat post-shock asystole while minimizing patient discomfort.

Certain post-shock sensing and post-shock pacing functions described herein may be cooperatively performed in control module 80, cardiac signal analyzer 90, therapy delivery module 84, electrical sensing module 86, and sensing and therapy delivery control parameters stored in memory 82. User-programmable control parameters may be programmed into memory 82 via telemetry module 88. Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40.

ECG episode data related to the detection of a shockable rhythm and the delivery of a CV/DF shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable rhythms, sensing cardiac signals, and delivering therapy.

Figure 4:
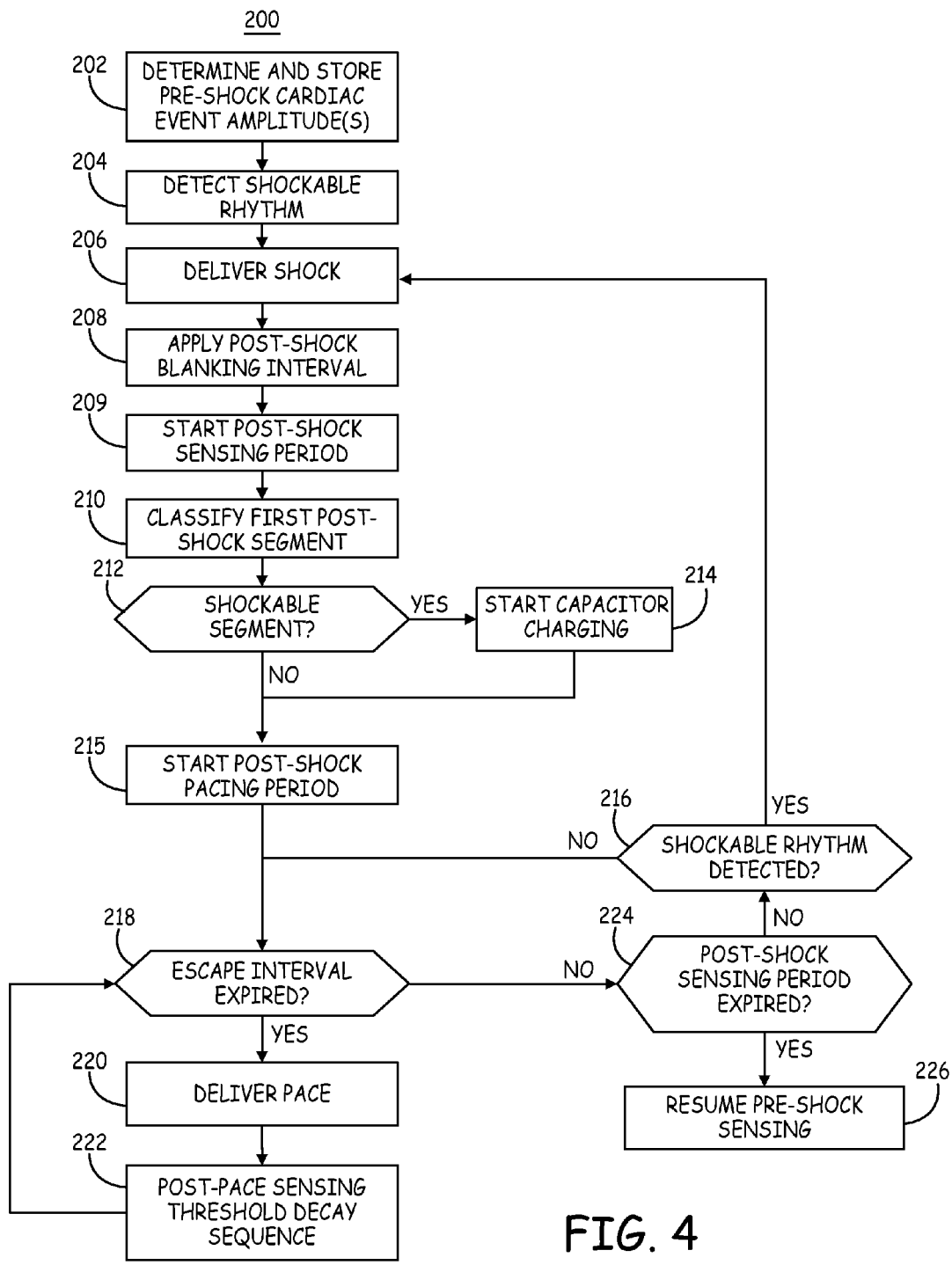
FIG. 4 is a flow chart of a method performed by the ICD of FIG. 1 for sensing cardiac events and delivering post-shock pacing pulses after delivering a cardioversion/defibrillation (CV/DF) shock pulse to the patient's heart.

FIG. 4 is a flow chart 200 of a method performed by ICD 14 for sensing cardiac events and delivering post-shock cardiac pacing. The methods disclosed in conjunction with the flow charts and timing diagrams presented herein are directed toward controlling an R-wave sensing threshold for sensing R-waves after delivery of a ventricular CV/DF shock and for controlling timing of ventricular pacing pulses during a post-shock pacing period. It is contemplated, however, that techniques disclosed herein may be implemented for sensing P-waves in an atrial chamber following delivery of post-shock pacing pulses and delivering post-shock atrial pacing pulses. Furthermore, aspects of the methods for controlling a post-pace cardiac event sensing threshold as disclosed herein may be implemented after delivering other types of electrical stimulation therapies, such as an anti-tachycardia pacing therapy, or tachyarrhythmia induction pulses or other types of electrical stimulation pulses. Accordingly, a post-pace decay sequence as described herein for controlling an auto-adjusting cardiac event sensing threshold may also be referred to as a "post-stimulation decay sequence" and may not be exclusively limited to post-shock pacing applications.

The cardiac sensing processes described in conjunction with flow chart 200 and other flow charts and timing diagrams presented herein are generally described for a given sensing channel 83 or 85 of sensing module 86. It is understood that the processes may be performed in conjunction with one sensing channel 83 or 85, but may be performed concomitantly in both sensing channels 83 and 85 in combination with control module 80 and cardiac signal analyzer 90.

Flow chart 200 is intended to illustrate the functional operation of ICD 14, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the ICD. Providing software, hardware, and/or firmware to accomplish the described functionality in the context of any modern ICD, given the disclosure herein, is within the abilities of one of skill in the art.

Methods described in conjunction with flow charts and timing diagrams presented herein may be implemented in a non-transitory computer-readable medium, e.g., included in memory 82, which includes instructions for causing a programmable processor to carry out the methods described. The instructions may be implemented as one or more software modules, which may be executed by themselves or in combination with other software.

At block 202, the ICD control module 80 determines a pre-shock (or more generally a pre-stimulation) cardiac event amplitude. In some instances, at least one pre-stimulation event amplitude is used for controlling a post-stimulation cardiac event sensing threshold, which may be a post-shock sensing threshold or a post-pace sensing threshold as described below, e.g., in conjunction with FIGS. 6 through 9. ICD control module 80 may determine a peak R-wave amplitude of a QRS morphology template determined by cardiac signal analyzer 90 and stored in memory 82. In some examples, a QRS morphology template is determined and stored for use in discriminating shockable and non-shockable rhythms. A QRS morphology template may be stored during a known rhythm, e.g., during a known paced or non-paced sinus rhythm, and compared to a cardiac electrical signal during an unknown rhythm. If the signal during the unknown rhythm matches the template, the unknown rhythm is detected as the rhythm corresponding to the template, e.g., a non-shockable sinus or other non-shockable, supra-ventricular rhythm.

If ICD 14 is configured to determine and store a QRS morphology template, a pre-shock R-wave amplitude may be determined from the QRS template, e.g., as a peak R-wave amplitude of a template of one or more intrinsically sensed heart beats originating in the atria in the absence of cardiac pacing. The pre-shock cardiac event amplitude may be measured from a filtered cardiac electrical signal that is filtered using the same filtering characteristics (e.g., filter bandpass) used by the respective sensing channel 83 or 85 for sensing cardiac events. Methods that may be used for automatically generating a non-paced R-wave template from which a pre-shock cardiac event amplitude may be determined are generally disclosed in U.S. Pat. No. 6,745,068 (Koyrakh, et al.), incorporated herein by reference in its entirety.

ICD control module 80 may additionally determine a peak amplitude of a P-wave morphology template determined by cardiac signal analyzer 90 during a known, non-shockable rhythm. The pre-shock P-wave amplitude and the pre-shock R-wave amplitude may both be determined and stored at block 202 and used by sensing module 86 in setting an initial value of a post-pace R-wave sensing threshold. The pre-shock cardiac event amplitude(s) may additionally or alternatively be used for detecting sensed events that meet escape interval reset criteria for resetting an escape interval described below.

In other examples, the pre-shock event amplitude may be determined from a peak amplitude of one or more cardiac events as they are sensed. For example, the pre-shock event amplitude may be determined as an average of the maximum peak amplitude of up to twelve consecutive or non-consecutive sensed events. The pre-shock event amplitude is determined to represent an expected cardiac event amplitude during a non-shockable rhythm in some examples. As such, the pre-shock event amplitude is typically determined during a non-shockable rhythm at block 202, not during a shockable rhythm detected immediately prior to delivering a shock. In other examples, the pre-shock event amplitude may be determined from cardiac events sensed just prior to detecting a shockable rhythm, which may be stored as a pre-episode signal sample. In still other examples, the pre-shock event amplitude may be determined from cardiac events sensed during an episode detected as a shockable rhythm.

The pre-shock event amplitude may be stored in memory 82 and may be updated whenever a QRS morphology template or P-wave template from which the event amplitude is derived is updated. If the pre-shock event amplitude is determined from cardiac events sensed prior to a shock therapy, the event amplitude may be updated on a regular periodic basis or as needed at block 202. For example, if the electrodes coupled to a given sensing channel 83 or 85 are changed, the pre-shock event amplitude is updated at block 202 to provide a relevant pre-shock event amplitude for a newly selected sensing vector. A pre-shock event amplitude may be updated after terminating a shockable rhythm, after anti-tachycardia pacing therapy or another therapy is delivered or a therapy adjustment is made, after ICD programming changes, or after any other ICD-related or other change, such as a prescription change, is made that may alter the amplitude of cardiac events being sensed by the sensing channels 83 and 85. Updates to the pre-shock event amplitude may be performed automatically by ICD 14 or triggered manually by a user interacting with external device 40.

At block 204, a shockable rhythm is detected by ICD 14. The initial shockable rhythm detection at block 204 occurs after a period of sinus rhythm, non-shockable supraventricular rhythm, or cardiac pacing. The shockable rhythm is detected using a detection algorithm implemented in ICD 14. The techniques disclosed herein for sensing and pacing during a post-shock time period are not limited to being practiced with a particular detection algorithm that is used for initial shockable rhythm detection, prior to delivering an initial CV/DF shock. Techniques disclosed in the above-incorporated patents may be used for initial shockable rhythm detection at block 204.

After a shockable rhythm is detected at block 204, a CV/DF shock is delivered at block 206. At block 208, a post-shock blanking interval is applied during which sensing module 86 is disabled from sensing cardiac events and producing cardiac event signals (or any produced cardiac event signals may be ignored by cardiac signal analyzer 90). The post-shock blanking interval is set to allow for post-shock electrode polarization recovery prior to re-enabling the sensing module 86 to sense cardiac events. The post-shock blanking interval is 1.5 seconds long in one example, but may be set to an interval greater than or less than 1.5 seconds depending on the time interval required for post-shock electrode polarization recovery in a given ICD system.

At block 209, a post-shock sensing period is started at the expiration of the blanking interval. During the post-shock sensing period, the cardiac event sensing threshold is controlled by sensing module 86 according to sensing control parameters which may distinctly define at least: a post-shock decay sequence used to sense the first intrinsic cardiac event after shock delivery; a post-sense decay sequence used to control the cardiac event sensing threshold after sensing a cardiac event during the post-shock sensing period, and a post-pace decay sequence used to control the cardiac event sensing threshold after delivering a pacing pulse during the post-shock pacing period. Automatic adjustment of the cardiac event sensing threshold during the post-shock sensing period is described in conjunction with FIGS. 8 through 10 below.

As shown in FIG. 4, the post-shock sensing period may be started prior to starting a post-shock pacing period in some examples. As described in conjunction with FIG. 5 below, the post-shock sensing period may include a first signal analysis segment followed by a post-shock pacing period. Cardiac pacing may be withheld during the first signal analysis segment but is enabled during the post-shock pacing period to treat post-shock asystole or post-shock bradycardia as needed. Cardiac events sensed during the post-shock sensing period are used for determining the need for another shock (in the case of shockable rhythm redetection) and for determining the need for post-shock pacing to treat asystole or bradycardia.

At block 210, cardiac signal analyzer 90 analyzes and classifies the first post-shock signal analysis segment of the cardiac electrical signal as a shockable or non-shockable segment based at least on cardiac events sensed during the signal analysis segment according to the post-shock sensing scheme. The signal analysis segment may be an n-second time interval during which R-wave sensing and/or morphology analysis is performed by sensing module 86 for determining whether the rhythm is shockable during the signal analysis segment. Therapy delivery module 84 may be disabled from delivering pacing pulses during the signal analysis segment. No post-shock pacing is delivered during at least an initial portion of the signal analysis segment to enable cardiac signal analyzer 90 to rapidly determine whether the signal analysis segment is a shockable segment. The control module 80 may control the therapy delivery module 84 to begin charging high voltage capacitors at block 214 in response to classifying the first post-shock signal analysis segment as a shockable segment at block 212.

The classification of the first signal analysis segment at block 212 as shockable or non-shockable may be a preliminary rhythm classification. High voltage capacitor recharging begins promptly in anticipation of redetection of a shockable rhythm based on the first signal analysis segment being classified as shockable. Cardiac signal analysis may continue after the first signal analysis segment for re-detecting a shockable rhythm at block 216 and delivering a shock at block 206 if needed.

In various examples, capacitor charging may be started at block 214 in response to at least one signal analysis segment meeting at least one shockable segment classification requirement, such as an estimated or actual cardiac cycle length being less than shockable segment threshold or limit. In other instances, capacitor charging is started at block 214 in response to at least two consecutive signal analysis segments meeting a shockable segment classification criterion, such as an estimated cycle length that is less than a VT/VF detection interval. Methods employed for controlling if and when capacitor charging is started may generally correspond to the techniques disclosed in U.S. Pat. application Ser. No. 14/519,220, incorporated herein by reference in its entirety.

Post-shock pacing is enabled at block 215 by starting the post-shock pacing period, which may be started upon expiration of the first signal analysis segment. In other examples, post-shock pacing may be enabled at block 215 at a selected time interval after shock delivery that is not limited to a starting or ending point of a signal analysis segment used for making a decision to start capacitor charging or redetecting a shockable rhythm. For example, if the first signal analysis segment is n-seconds long, post-shock pacing may be enabled to begin at m-seconds after shock delivery, which may be during or after the n-second segment. In some instances, capacitor charging may start at block 214 concurrently with the start of the post-shock pacing period. In other instances, capacitor charging may start at or during the post-shock pacing period or not at all. For example, the post-shock pacing period may be started at block 215 during or upon expiration of the first signal analysis segment, and the decision to start capacitor charging may require that at least two signal analysis segments are classified as shockable before starting capacitor charging.

In some instances, the first signal analysis segment is an n-second segment, e.g., a six-second segment, over which a cardiac event cycle length is determined or estimated based upon R-wave sense event signals produced during the entire n-second segment. Morphology analysis is performed over all of or less than the entire n-second segment, e.g., the last three seconds of a six-second segment. The segment is classified as shockable or non-shockable at the expiration of the segment based on both the actual or estimated cycle length and the morphology analysis. As such, capacitor charging may begin at block 214 as early as 7.5 seconds after shock delivery in this illustrative example (1.5 second post-shock blanking period plus six-second signal analysis segment). The post-shock pacing period, however, may begin mid-way through the six-second signal analysis segment, beginning at 4.5 seconds post-shock, to deliver pacing pulses as needed.

If therapy delivery module 84 is configured to generate and deliver CV/DF shocks and post-shock pacing pulses using the HV therapy delivery module, post-shock pacing may be suspended at some point during capacitor charging started at block 214. In other instances, post-shock pacing may continue as needed during capacitor charging and until the post-shock pacing period ends or a shockable rhythm is detected.

Figure 5:
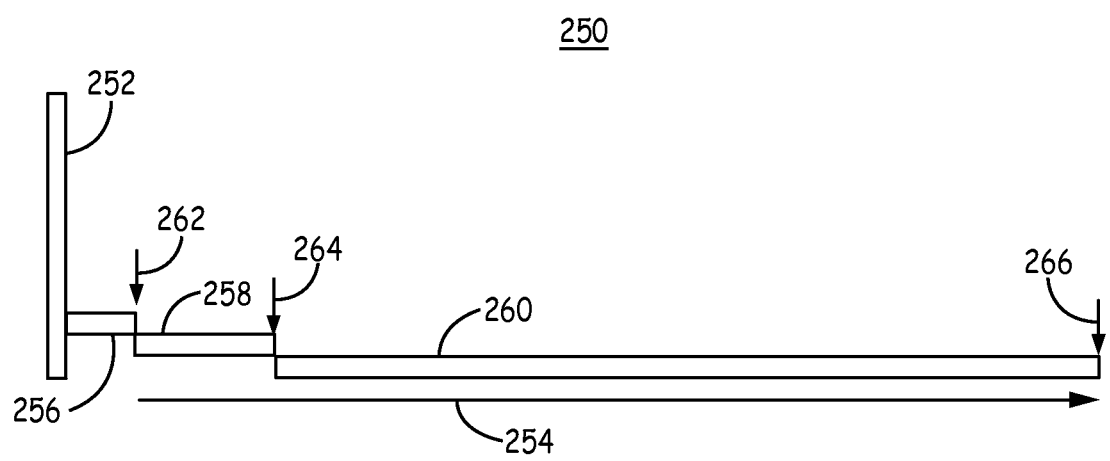
FIG. 5 is a conceptual diagram of a post-shock sensing period a CV/DF shock pulse according to one example.

The post-shock sensing period started at block 209 encompasses the post-shock pacing period started at block 215 in some examples and as shown in FIG. 5. Cardiac signal analyzer 90 senses cardiac signals during the post-shock sensing period for use in determining a need for post-shock pacing based on an expired escape interval as indicated at block 218. If an escape interval started during the post-shock sensing period expires (before or after the start of the post-shock pacing period), as determined at block 218, a post-shock pacing pulse may be delivered at block 220 at or after the onset of the post-shock pacing period. Control of an escape interval timer in response to cardiac sensed events during the post-shock pacing period is described below, e.g., in conjunction with FIGS. 8 and 10.

Cardiac signals sensed during the post-shock sensing period are also used for re-detecting a shockable rhythm at block 216.

If a pacing pulse is delivered at block 220, the sensing module 86 adjusts the R-wave sensing threshold at block 222 according to a post-pace sensing threshold decay sequence after delivering a pacing pulse. Cardiac events sensed during the post-pace sensing threshold decay sequence (block 222) are analyzed by cardiac signal analyzer 90 for use in controlling an escape interval timer and delivery of post-shock pacing pulses. The steps performed in blocks 218, 220 and 222 are described in further detail in flow chart 300 of FIG. 6.

Cardiac signal analyzer 90 continues to analyze sensed cardiac events for determining whether to reset the escape interval timer at block 218 until the post-shock sensing period expires at block 224, or until a shockable rhythm is redetected at block 216. The post-shock sensing period may be up to 30 seconds long, up to one minute long, or other predetermined time period. When the post-shock sensing period expires, normal pre-shock cardiac event sensing resumes at block 226 according to pre-shock sensing control parameters.

FIG. 5 is a conceptual diagram 250 of a post-shock sensing period 254 following a CV/DF shock pulse 252. The shock pulse 252 is immediately followed by a post-shock blanking interval 256 during which cardiac event sensing is disabled to allow post-shock electrode polarization recovery. At the expiration 262 of blanking interval 256, a cardiac signal analysis segment 258 is started, and cardiac event sensing is enabled. Post-shock pacing is disabled during signal analysis segment 258 (and blanking interval 256). Cardiac events and/or the cardiac signal morphology are analyzed over the analysis segment 258 for classifying the segment 258 as shockable or non-shockable. Pacing escape intervals may be set in response to sensed events, but pacing pulses are not delivered during segment 258. In some examples, no pacing pulses are delivered during the signal analysis segment 258 to allow a determination of actual or estimated cycle lengths to be made for contributing to a decision to begin capacitor charging.

At the expiration 264 of signal analysis segment 258, a segment classification is produced (shockable or non-shockable) by cardiac signal analyzer 90 based on an analysis of the cardiac electrical signal during segment 258. In one example, the ventricular cycle length is estimated in response to a count of sensed R-waves during the segment 258 and contributes to the segment classification. At signal analysis segment expiration 264, high voltage capacitor charging may be started in response to a shockable classification of the analysis segment 258. In one example, with no limitation intended, the post-shock blanking period is 1.5 seconds and the initial signal analysis segment 258 is 3 seconds. Accordingly, for the first 4.5 seconds post-shock, no post-shock pacing is delivered, but capacitor charging may be started as early as 4.5 seconds post-shock in preparation for another CV/DF shock if needed.

At the expiration 264 of signal analysis segment 258, post-shock pacing is enabled. A post-shock pacing period 260 extends from the end 264 of signal analysis segment 258 until the expiration 266 of the post-shock sensing period 254. During the post-shock pacing period 260, the cardiac event sensing threshold for each sensing channel 83 and 85 is automatically adjusted by the sensing module 80 according to either a post-pace decay sequence or a post-sense decay sequence, both of which may be modified from a pre-shock decay sequence used to control the cardiac event sensing threshold prior to shock pulse 252. As described below, the post-pace decay sequence is used by sensing module 86 following delivery of a post-shock pacing pulse by therapy delivery module 84, and a post-sense decay sequence is used after an intrinsic cardiac event is sensed by sensing module 86.

Sensing control parameters used by sensing module 86 to automatically adjust the cardiac event sensing threshold during post-shock pacing period 260 may be different that sensing control parameters used to automatically adjustment the cardiac event sensing threshold during the signal analysis segment 258. For example, the sensing module 86 uses a post-pace decay sequence during post-shock pacing period 260 that is not utilized during signal analysis segment 258 since pacing is disabled during the signal analysis segment. The post-sense decay sequence used to control automatic adjustment of the cardiac event sensing threshold during the pacing period 260 may be the same or similar to a decay sequence used after sensing an intrinsic event during the signal analysis segment 258.

Cardiac events sensed during the signal analysis segment 258 and during post-shock pacing period 260 are used for determining a need for post-shock pacing that begins during post-shock pacing period 260. For example, if a pacing escape interval has expired during signal analysis segment 258 prior to the expiration 264 of segment 258, and another R-wave sense event has not been received by cardiac signal analyzer 90 to cause timing circuit 92 to start a new pacing escape interval, a post-shock pacing pulse may be delivered at 264 upon starting post-shock pacing period 260.

Additionally, cardiac events sensed during pacing period 260 may be used for redetecting a shockable rhythm. The classification of signal analysis segment 258, cardiac events sensed during post-shock pacing period 260, and signal morphology analysis during post-shock pacing period 260 may be used in any combination according to a re-detection algorithm. Detection of a shockable rhythm may occur during post-shock pacing period 260 resulting in shock delivery prior to the expiration of the pacing period 260.

In some examples, post-shock pacing period 260 is divided into cardiac signal analysis segments for the purposes of redetecting a shockable rhythm post-shock. For example, if the post-shock sensing period 254 is 30 seconds long, the initial signal analysis segment 258 may be a 3-second segment followed by nine more 3-second segments during post-shock pacing period 260. Each segment may be classified as a shockable or non-shockable segment at its expiration. If at least two out of three of the most recent consecutive segments are classified as shockable, for example, the control module 80 may enable the therapy delivery module 84 to deliver a shock. Accordingly, post-shock pacing period 260 may be terminated early, e.g., at the expiration of an n-second signal analysis segment. If two out of three shockable segments are required for detecting a shockable rhythm the post-shock pacing period may be at least 6 seconds long when the signal analysis segments are three seconds long.

In other examples, sensed cardiac events and cardiac signal morphology may be analyzed without requiring classification of n-second segments during the post-shock sensing period 254. For example, sensed cardiac events, event intervals, and cardiac signal morphology may be performed in an ongoing, beat-by-beat until shockable rhythm redetection criteria are satisfied or until the post-shock sensing period 254 expires. The ICD 14 may then resume normal pre-shock sensing and shockable rhythm detection.

During the post-shock pacing period 260, the timing circuit 92 controls an escape interval timer in response to paced and sensed events. Pacing pulses will start a pacing escape interval. Sensed events that meet escape interval reset criteria will restart the escape interval timer. In some examples, all sensed events (outside of a blanking interval) may be used in an algorithm for detecting a shockable rhythm during the post-shock pacing period 260. Not all sensed events, however, will cause an escape interval to be restarted. A sensed cardiac event is analyzed by cardiac signal analyzer to determine if reset criteria are met. If not, the sensed cardiac event does not cause the escape interval timer to be restarted, but may be used for redetecting a shockable rhythm. The cardiac event sensing threshold is automatically adjusted according to a decay sequence that allows sensing of low amplitude fibrillation waves as well as higher amplitude R-waves so events required for detecting a shockable rhythm are sensed as well as events that are used on controlling pacing pulse delivery.

The various time intervals including blanking interval 256, signal analysis segment 258, post-shock sensing period 254, and/or post-shock pacing period 260 may be controlled by timing circuit 92. At the expiration 266 of the post-shock sensing period 254, the post-shock pacing period 260 is terminated. ICD 14 may resume normal pre-shock sensing that includes a pre-shock decay sequence used to control the cardiac event sensing threshold by sensing module 86. In other examples, the post-shock pacing period 260 and the post-shock sensing period 254 may not have fixed end points. If the rhythm has not returned to a non-shockable rhythm at cycle lengths that are longer than VT/VF detection intervals, the post-shock sensing period may be extended. Post-shock pacing may continue as long as asystole is being detected or up to some maximum time limit.

Figure 6:
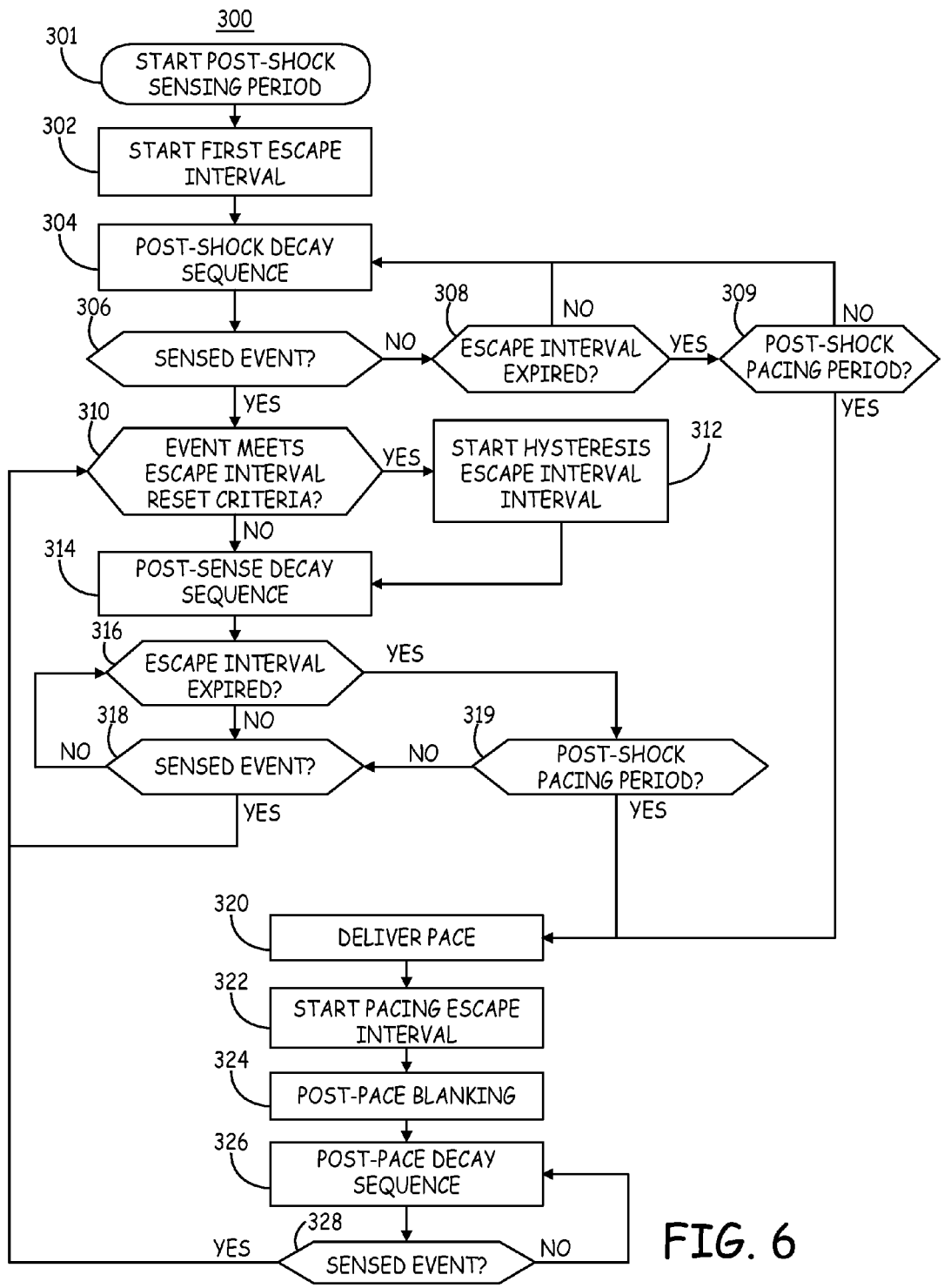
FIG. 6 is a flow chart of a method for controlling pacing pulses during the post-shock pacing period of FIG. 5 according to one example.

FIG. 6 is a flow chart 300 of a method for controlling cardiac event sensing during the post-shock sensing period 254 and for controlling pacing pulse delivery during the post-shock pacing period 260 of FIG. 5. Steps described in flow chart 300 relate to the sensing and pacing control operations performed during the process of flow chart 200 of FIG. 4, and some steps may correspond to steps 218, 220 and 222 of FIG. 4. ICD 14 may exit the method of flow chart 300 when the post-shock pacing period 260 and/or post-shock sensing period 254 ends, or when ICD 14 redetects a shockable rhythm during the post-shock sensing period 254.

In some examples, upon starting the post-shock sensing period at block 301, timing circuit 92 sets the pacing escape interval timer to start running a first escape interval at block 302. The first escape interval is set to provide post-shock pacing in the presence of asystole (or bradycardia) or low amplitude R-waves that are not occurring at a fast, shockable rhythm interval, e.g., a VT or VF interval of 300 ms or less. The first escape interval started at block 302 may be started at the end of the post-shock blanking period 256 (FIG. 5), i.e., the start of post-shock sensing period 254 and the first signal analysis segment 258. However, pacing pulses will not be delivered during signal analysis segment 258. Alternatively, the first escape interval may be started at the onset 264 of post-shock pacing period 260 or one escape interval prior to the onset 264 of post-shock pacing period 260.

The first escape interval started at block 302 may range from 1,000 ms to 3,000 ms in some examples. In one instance, the first escape interval started at block 302 is 1200 ms, however shorter or longer escape intervals may be used to maintain a minimum heart rate once the post-shock pacing period 260 begins. As described below, if the first escape interval started at block 302 expires before the post-shock pacing period 260 begins, and a new escape interval has not been restarted, a pacing pulse is withheld until the start of the post-shock pacing period 260. This situation of the first escape interval expiring before the post-shock pacing period starts may arise when the first escape interval started at the onset of the post-shock sensing period 254 is shorter than the first signal analysis segment 258. For example, if the first escape interval is 1200 ms but signal analysis segment 258 is 3 seconds and the post-shock pacing period 260 begins at the expiration of the signal analysis segment 258, the first escape interval may expire prior to the start of the post-shock pacing period 260. If this happens, the scheduled pacing pulse may be withheld until the post-shock pacing period 260 is started, pending no intervening sensed events meeting escape interval reset criteria.

In other examples, the first escape interval started at block 302 may be set equal in time to the first signal analysis segment 258 or equal to the time interval between the end of the post-shock blanking interval 256 and the start of the post-shock pacing period 260, effectively inhibiting pacing until the post-shock pacing period 260 begins. For example, the first escape interval may be set to 3,000 ms at block 302 when the first signal analysis segment 258 is 3 seconds long. If the first escape interval expires without a sensed event, the first post-shock pacing pulse is delivered at the expiration of the first escape interval, coincident with the start of the post-shock pacing period 260.

Upon starting the escape interval at block 302, the sensing module 86 starts a post-shock decay sequence at block 304, which may utilize sensing control parameters stored in memory 82, for controlling the cardiac event sensing threshold. The first post-shock decay sequence may include setting the initial sensing threshold amplitude based on a stored pre-shock cardiac event amplitude. The cardiac event threshold decays according to a first post-shock decay sequence until the first post-shock cardiac event is sensed at block 306. The first post-shock decay sequence used to sense the first cardiac event after shock delivery may correspond to the first post-shock decay sequence disclosed in the above-incorporated U.S. Pat. application Ser. No. 14/519, 220.

The first post-shock decay sequence may include setting the R-wave sensing threshold to an initial amplitude based on a stored pre-shock R-wave amplitude determined prior to shock delivery, such as 30% of an R-wave amplitude of a supraventricular rhythm template stored for use in detecting and discriminating shockable and non-shockable rhythms. The initial threshold may be limited to a pre-defined maximum initial sensing threshold. In one example, the post-shock R-wave sensing threshold immediately begins to decay from the initial amplitude according to a first decay rate over a step drop interval until it reaches an intermediate threshold amplitude, after which it decays at a second decay rate until reaching a sensing floor.

For instance, the first decay rate may be a rate of 20% per second of the pre-shock R-wave peak amplitude used to set the initial post-shock sensing threshold amplitude. The step drop interval may be 500 ms. Upon expiration of the drop interval, the post-shock R-wave sensing threshold may be adjusted by a step drop to an intermediate R-wave amplitude and start decreasing at a second decay rate. In some instances the step drop may only be a change in decay rate without a step change in R-wave sensing threshold amplitude. In the illustrative example, when the initial sensing threshold amplitude is set to 30% of a stored pre-shock maximum peak R-wave amplitude and the first decay rate is 20% of the stored maximum peak R-wave amplitude per second, the R-wave sensing threshold will reach 20% of the stored maximum peak R-wave amplitude in 500 ms. The intermediate threshold amplitude to which the sensing threshold is adjusted to at the step drop time may be set to 20% of the stored maximum peak R-wave amplitude. As a result, the R-wave sensing threshold amplitude reaches the intermediate amplitude at the expiration of the step drop interval. The first decay rate is changed to the second decay rate at the expiration of step drop interval. In one example, the second decay rate during the first post-shock decay sequence is 100% per second of the maximum peak R-wave amplitude used to set the initial sensing threshold amplitude. An R-wave sense event signal is produced by sensing module 86 when the filtered, rectified cardiac signal crosses R-wave sensing threshold.

In some instances, the second decay rate may reach a sensing floor before the cardiac signal crosses the R-wave sensing threshold during the first post-shock decay sequence. The sensing floor is a minimum sensing threshold amplitude that, if reached during the second decay rate, is held constant until the cardiac signal crosses the R-wave sensing threshold. The sensing floor may be 15 to 25 μV in some examples.

If the first escape interval started at block 302 expires without sensing an event prior to starting the post-shock pacing period 260 (FIG. 5) as determined at blocks 306, 308 and 309, a pacing pulse is not immediately delivered. The sensing module 86 continues controlling the cardiac event sensing threshold according to the first post-shock decay sequence until an event is sensed at block 306 or the post-shock pacing period 260 is started. If the escape interval is expired ("yes" branch of block 308) and the post-shock pacing period is started ("yes" branch of block 309), a pacing pulse is delivered at block 320. As described above, the first escape interval started at block 302 may expire prior to starting the post-shock pacing period 260. If a new pacing escape interval has not been started in response to a sensed event, a post-shock pacing pulse may be delivered at the onset 264 of post-shock pacing period 260.

If a cardiac event is sensed at block 306 during the first escape interval started at block 302, cardiac signal analyzer 90 determines if the sensed event meets escape interval reset criteria at block 310. During the post-shock sensing period 254, not all sensed events will cause the timing circuit 92 to reset the pacing escape interval timer. In one example, the reset criteria include an amplitude requirement greater than the cardiac event sensing threshold. In another example, the reset criteria include a sensed cardiac event interval that is shorter than a predefined VT or VF detection interval. Reset criteria are described below in conjunction with FIGS. 8 and 10.

If the reset criteria are not met, the escape interval continues running, and the sensing module 86 adjusts the cardiac sensing threshold according to a post-sense decay sequence started at block 314 in response to the sensed event. After sensing the first post-shock cardiac event during the first post-shock decay sequence, sensing module 86 adjusts the cardiac event sensing threshold according to a post-sense decay sequence as described below in conjunction with FIG. 8. The post-sense decay sequence may correspond to the second post-shock decay sequence disclosed in the above-incorporated U.S. Pat. application Ser. No. 14/519,220.

If reset criteria are met at block 310 in response to a sensed event at block 306, the timing circuit 92 resets the escape interval timer at block 312, and the sensing module 86 starts the post-sense decay sequence at block 314. The escape interval timer may be reset to a hysteresis escape interval at block 312 in response to the sensed event meeting the reset criteria at block 310. The hysteresis escape interval may be longer than the first escape interval set at block 302 or a pacing escape interval started in response to a pacing pulse in order to allow a return of the intrinsic rhythm to drive the heart rate rather than a programmed post-shock pacing rate.

In the post-sense decay sequence started at block 314, the initial sensing threshold amplitude is set based on the maximum peak amplitude of the most recently sensed event. The post-sense decay sequence is employed by sensing module 86 to control the automatically-adjusted sensing threshold after sensed events that occur during the post-shock sensing period 254, i.e., during the first signal analysis segment 258 and post-shock pacing period 260.

If the currently running escape interval has not expired (at block 316), and cardiac signal analyzer 90 receives a sense event signal at block 318 during the post-sense decay sequence, cardiac signal analyzer 90 returns to block 310 to determine if the event meets the escape interval reset criteria at block 310. As long as the escape interval does not expire at block 316, the sensing module 86 may continue sensing events using the post-sense decay sequence. If those sense events do not cause the reset criteria to be met, the escape interval continues running. Accordingly, multiple sense event signals could occur during the currently running escape interval without causing the escape interval to be reset. This situation is shown and described below in conjunction with FIG. 10.

In some examples, an event that is sensed outside any applicable blanking interval will cause the escape interval timer to be reset only if the event meets the reset criteria. In some applications, a post-sense refractory period may be applied following a sensed event. In these applications, a non-refractory sense event may not cause the escape interval timer to be reset unless reset criteria are also met. In other examples, a refractory sense event may cause the escape interval timer to be reset if reset criteria are met by the sense event. In other words, the escape interval timer may be reset in response to any non-blanking period sense event that meets reset criteria independent of any defined post-sense refractory period in some examples.

If the currently running escape interval expires and the post-shock pacing period has started, as determined at blocks 316 and 319, a pacing pulse is delivered at block 320. Otherwise, if the post-shock pacing period has not been started ("no" branch of block 319) the post-sense decay sequence that was started at block 314 continues until the cardiac signal crosses the sensing threshold at block 318 starting a new post-sense decay sequence at block 314 (and new hysteresis escape interval at block 312 if reset criteria are met).

In response to pacing pulse delivery at block 320, the timing circuit 92 starts a pacing escape interval at block 322. The pacing escape interval started after a pacing pulse may be on the order of 1,000 ms to 1,500 ms, and is nominally 1,200 ms in one example. The pacing escape interval started at block 320 in response to a pacing pulse is shorter than the hysteresis escape interval started at block 312 in response to sensed events.

A post-pace blanking interval may be applied at block 324 to allow for recovery from electrode polarization due to the pacing pulse. After the blanking interval, a post-pace decay sequence is started at block 326 by sensing module 86 for controlling the cardiac event sensing threshold after the pacing pulse. If cardiac signal analyzer 90 receives a sense event signal during the pacing escape interval, at block 328, the process returns to block 310 to determine if the sensed event meets escape interval reset criteria. This process continues for the duration of the post-shock pacing period 260, which may expire at the end of the post-pace sensing period 254 or upon shockable rhythm detection, whichever occurs earlier.

Figure 7:
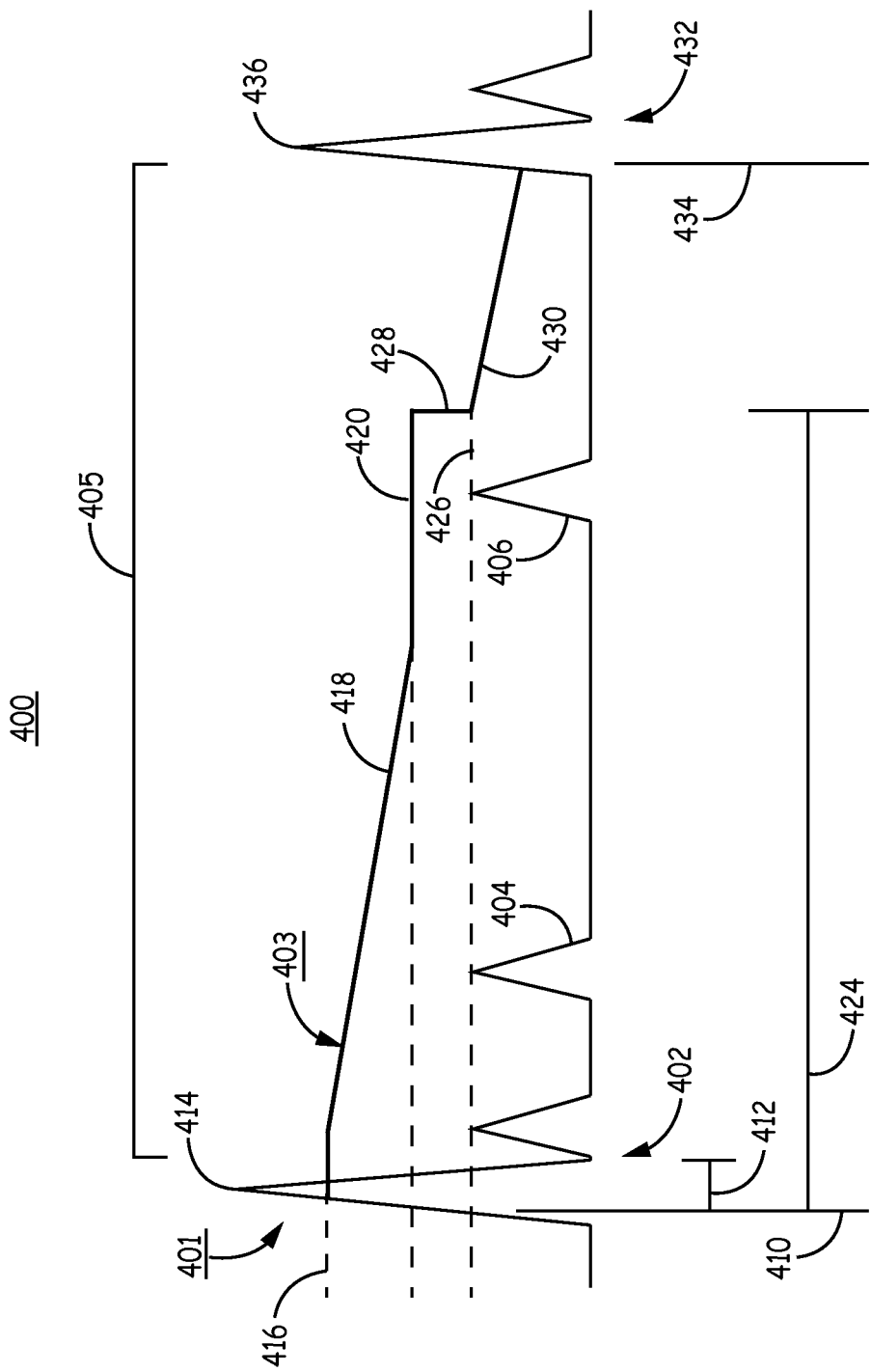
FIG. 7 is a diagram of a cardiac electrical signal and an automatically adjusted pre-shock R-wave sensing threshold.

FIG. 7 is a conceptual diagram 400 of a rectified cardiac electrical signal 401, e.g., an ECG, received by ICD sensing module 86 and an automatically adjusted pre-shock R-wave sensing threshold 403. The example shown and described in conjunction with FIG. 7 is an illustrative example of one pre-shock decay sequence that could be used for sensing events for controlling bradycardia pacing and detecting shockable rhythms by ICD 14 prior to delivering a shock. Numerous variations of a pre-shock decay sequence may be conceived, however, the example shown here is used to illustrate differences between sensing control parameters used to automatically adjust the pre-shock R-wave sensing threshold 403 and sensing control parameters used to automatically adjust a post-pace R-wave sensing threshold as described below.

The cardiac electrical signal 401 includes a QRS complex 402, T-wave 404, P-wave 406 and a next QRS complex 432. The cardiac signal 401 is first passed through a bandpass filter (e.g., passing 10 Hz to 32 Hz) and is then rectified so that only positive deflections remain as shown in FIG. 7. An R-wave sense event signal 410 is produced when the R-wave of the first QRS complex 402 crosses a sensing threshold (not illustrated). A post-sense blanking interval 412 is applied to the sensing module 86 after R-wave sense event signal 410. The post-sense blanking interval 412 may be in the range of 150 ms to 180 ms in some examples, but may be set to longer or shorter intervals as needed to avoid sensing the same QRS complex 402 twice.

The R-wave maximum peak amplitude 414 may be determined after the R-wave sense event signal 410, e.g., during blanking interval 412, and used to set the initial amplitude 416 of the R-wave sensing threshold 403 during the succeeding cardiac cycle. After post-sense blanking interval 412, the R-wave sensing threshold 403 is automatically adjusted according to a pre-shock decay sequence 405. The R-wave sensing threshold 403 begins at the initial amplitude 416 and decays at a first, pre-shock decay rate 418. The R-wave sensing threshold 403 decays at the first pre-shock decay rate 418 until it reaches an intermediate threshold amplitude 420, which may be a predetermined percentage of the maximum peak amplitude 414 of the most recently sensed R-wave.

In one example, the pre-shock sensing threshold 403 has a starting amplitude 416 set to a first predetermined percentage, e.g., 60%, of the most recent R-wave peak amplitude 414. The pre-shock first decay rate 418 is set such that the sensing threshold 403 decays at a rate of 35% (of the peak R-wave amplitude 414) per second in the example shown. The first decay rate 418 is applied over a drop interval 424 which is a predetermined time interval. If the sensing threshold 403 reaches a predetermined intermediate amplitude 420 within the drop interval 424, the sensing threshold 403 is held at the predetermined amplitude 420 until the drop interval 424 expires. In one example, the predetermined intermediate amplitude 420 is 30% of the most recent R-wave peak amplitude 414.

The pre-shock drop interval 424 may be started when the R-wave sense event signal 410 is produced or upon expiration of blanking interval 412. The pre-shock drop interval 424 is 1.5 seconds in one example. The first decay rate 418, the predetermined intermediate amplitude 420, and the drop interval 424 are pre-shock sensing control parameters that are selected to prevent the R-wave sensing threshold 403 from falling below an expected amplitude of the T-wave 404 and P-wave 406, which could otherwise result in oversensing of T-waves and/or P-waves as false R-wave sense events. After the pre-shock drop interval 424 expires, the R-wave sensing threshold 403 is adjusted by a step-drop 428 to a second predetermined intermediate amplitude 426 of the R-wave peak amplitude 414. In one example, the second predetermined intermediate amplitude 426 is 20% of the R-wave peak amplitude 414.

After the step-drop 428, the R-wave sensing threshold 403 starts a second pre-shock decay rate 430. This second pre-shock decay rate 430 continues until the cardiac signal 401 crosses the R-wave sensing threshold 403, producing the next R-wave sense event signal 434, or until the R-wave sensing threshold 403 reaches a sensing threshold floor. The sensing threshold floor is a minimum sensing threshold amplitude, e.g., 25 µV or less. If the cardiac signal 401 does not cross the R-wave sensing threshold 403 during the second pre-shock decay rate 430, the R-wave sensing threshold will remain at the sensing floor until the cardiac signal 401 crosses the sensing floor (or until an escape interval expires resulting in a pacing pulse).

The time interval from the first R-wave sense event signal 410 to the next R-wave sense event signal 434 is measured as an RR interval and used for detecting and discriminating shockable and non-shockable rhythms in accordance with an implemented detection algorithm. The next R-wave sense event signal 434 starts the next pre-shock blanking interval and next pre-shock drop interval (not illustrated though analogous to intervals 412 and 424 respectively). The R-wave peak amplitude 436 of the sensed QRS complex 432 is used to set the next initial R-wave sensing threshold of the next pre-shock decay sequence. It is recognized that a pre-shock R-wave sensing threshold 403 may be automatically adjusted according to a pre-shock decay sequence 405 that includes various criteria for setting at least the initial amplitude and one decay rate and may include one or more intermediate amplitudes, two or more decay rates, and one or more drop intervals.

FIG. 8 is a timing diagram 500 illustrating a filtered and rectified cardiac signal 501, an automatically adjusted R-wave sensing threshold 540, and R-wave sense event signals 551. A post-shock pacing pulse 504 is delivered causing a large deflection 502 of the cardiac signal 501. The timing circuit 92 starts a pacing escape interval 524 in response to the pacing pulse 502. The timing circuit 92 starts a post-pace blanking interval 520 upon pacing pulse delivery that disables sensing module 86 from producing cardiac event signals during the blanking interval 520. The blanking interval 520 is 500 ms in one example and is provided to allow recovery from post-pace electrode polarization before cardiac event sensing is resumed. A post-pace decay sequence 530 is started upon expiration of the blanking interval 520. The post-pace decay sequence 530 starts with an R-wave sensing threshold 540, which is set to an initial amplitude 542 that is based on one or more stored pre-shock cardiac event amplitudes.

The pre-shock R-wave amplitude (Rpeak) 532 and the pre-shock P-wave amplitude (Ppeak) 534 are indicated. These values are stored in memory 82 at block 202 of FIG. 4. In one example, the initial amplitude 542 of R-wave sensing threshold 540 during post-pace decay sequence 530 is selected from a predetermined percentage of Rpeak 532 and a predetermined percentage Ppeak 534. The initial threshold 542, for example, is set to 30% of Rpeak 532, 10% of Rpeak 532, 200% of Ppeak 534, or another selected percentage of Rpeak 532 or Ppeak 534.

The initial threshold 542 may be selected based on analysis of both the pre-shock R-wave amplitude and the pre-shock P-wave amplitude stored at block 202 of FIG. 4. For example, the starting threshold 542 may be selected as a mean or median value of at least two different predetermined percentages of the stored cardiac event amplitudes. To illustrate, 30% of the Rpeak 532 (0.3*Rpeak), 10% of Rpeak (0.1*Rpeak), and twice Ppeak (2*Ppeak) may each be determined. The initial amplitude 542 of R-wave sensing threshold 540 is selected as the median value of the determined percentage values (0.3*Rpeak, 0.1*Rpeak and 0.2*Ppeak). In the example shown, starting amplitude 542 is set to 2*Ppeak which is the median value of 0.3*Rpeak, 2*Ppeak and 0.1*Rpeak.

In some cases if the stored cardiac event peak amplitude (Rpeak 532 or Ppeak 534) exceeds an amplitude limit, the amplitude limit is substituted for the stored peak cardiac event amplitude for determining the specified percentages of that cardiac event amplitude. To illustrate, an R-wave amplitude limit may be set to 3 mV. If Rpeak 532 exceeds the amplitude limit, 30% and 10% of the amplitude limit, i.e., 30% and 10% of 3 mV, are substituted for 0.3*Rpeak and 0.1*Rpeak.

FIG. 9 is an enlarged view of a portion of the post-pace decay sequence 530 illustrating R-wave sensing threshold 540 as it is adjusted from the initial amplitude 542 to an amplitude floor 548 according to post-pace sensing control parameters. The post-pace sensing control parameters include a drop time interval 522, an intermediate threshold 544, and a decay rate 546. The R-wave sensing threshold 540 is maintained at the initial amplitude 542 from the expiration of post-pace blanking interval 520 to the expiration of drop time interval 522. In one example, drop time interval 522 is 700 ms from the pacing pulse 502 or 200 ms from the expiration of the post-pace blanking interval 520. The drop time interval 522 is shorter than the drop time interval 424 used during pre-shock decay sequence 405. Both the initial and intermediate thresholds 542 and 544 are relatively less than the initial and intermediate thresholds 416 and 420 of the pre-shock decay sequence 405 to enable sensing of fine VF or other low amplitude ventricular electrical activity post-shock.

The R-wave sensing threshold 540 is adjusted in a step-change from the initial threshold 542 to the intermediate threshold 544 at the expiration of drop time interval 522. In other examples, a decay rate may be specified for adjusting from initial threshold 542 to intermediate threshold 544. The intermediate threshold 544 may be set as a percentage of the starting threshold 542, a percentage of Rpeak 532, Ppeak 534 or a value selected from one or more percentages of Rpeak 532 and Ppeak 534. In one example, 20% of Rpeak 532 (0.2*Rpeak), 10% of Rpeak 532 (0.1*Rpeak) and 125% of Ppeak 534 (1.25*Ppeak) are each determined Intermediate threshold 544 is selected as the median of the determined 0.2*Rpeak, 0.1*Rpeak and 1.25*Ppeak. As described above, an amplitude limit may be substituted for Rpeak 532 if Rpeak 532 exceeds the amplitude limit.

The R-wave sensing threshold 540 is adjusted from the intermediate threshold 544 to the amplitude floor 548 according to a post-pace decay rate 546. Decay rate 546 may be 100% of the initial amplitude 542 per second. If the amplitude floor 548 is reached prior to sensing an event during decay sequence 530, the sensing threshold 540 remains at the amplitude floor 548 until the cardiac signal 501 crosses the amplitude floor 548 or the pacing escape interval 524 expires.

The R-wave sensing threshold 540 shown in FIG. 9 adjusted according to post-pace decay sequence 530 is described in the context of post-shock pacing pulse used to treat asystole. It is contemplated that the post-pace decay sequence 530 may be used for adjusting a cardiac event sensing threshold following other types of electrical stimulation pulses that are delivered to a patient's heart, including an anti-tachycardia pacing pulse or a bradycardia pacing pulse.

The post-pace decay sequence 530, or the first post-shock decay sequence described in conjunction with block 304 of FIG. 6, may be used following any large stimulation pulse after which rapid recovery of sensing is required. Such large stimulation pulses may include therapeutic pulses (such as a CV/DF shock or pacing pulse) and non-therapeutic pulses (such as an induction shock delivered to induce VT or VF during ICD testing). Relatively large stimulation pulses may be delivered transthoracically, using extracardiac electrodes such as the suprasternal or substernal electrodes 24, 28 and 30 shown in FIGS. 1 and 2. Transthoracic stimulation pulses are relatively higher in energy than cardiac stimulation pulses that are delivered using electrodes that are more proximal to or in contact with the myocardium. The post-pace decay sequence 530 or the above-described first post-shock decay sequence, which may be used alone, together and/or in combination with the post-sense decay sequence 552, may be used any time discrimination between fine VF and asystole is required for controlling appropriate therapy delivery (e.g., a shock vs. pacing).

Referring again to FIG. 8, if the pacing escape interval 524 expires, a pacing pulse 514 is delivered, causing cardiac signal deflection 512. The timing circuit 92 starts a pacing escape interval 524'. The sensing module 86 starts a post-pace blanking interval 520' and a drop time interval 522' in accordance with the sensing control parameters defining post-pace decay sequence 530. The sensing module 86 controls the R-wave sensing threshold 540 according to the post-pace decay sequence 530' beginning upon the expiration of the post-pace blanking interval 520'. As described above, the post-pace decay sequence 530' includes initial amplitude 542, intermediate amplitude 544, decay rate 546 and amplitude floor 548 as shown in FIG. 9. Post-pace decay sequence 530' is terminated prematurely in this example when the filtered, rectified cardiac signal 501 crosses the R-wave sensing threshold 540 outside a post-sense blanking interval 565 but early in the decay sequence 530' before drop time interval 522' expires. The sensing module 86 produces an R-wave sense event signal 554 that is passed to cardiac signal analyzer 90.

In response to receiving R-wave sense event signal 554, cardiac signal analyzer 90 determines if the sensed event 558 meets escape interval reset criteria. In one example, a maximum peak amplitude of sensed event 558 is determined during blanking interval 565 in response to R-wave sense event signal 554. If the peak amplitude of sensed event 558 exceeds an escape interval reset amplitude 560, the pacing escape interval 524' that was started upon delivery of pacing pulse 512 is terminated. Timing circuit 92 resets the escape interval timer to a hysteresis escape interval 528 in response to R-wave sense event signal 554.

The escape interval reset amplitude 560 applied to sensed event 558 may be based on Rpeak 532 and/or Ppeak 534. In the example shown, escape interval reset amplitude 560 is set to twice Ppeak 534. In other examples, reset amplitude 560 may be set to a fixed difference from Rpeak 532; a fixed difference from Ppeak 534; a percentage of Rpeak 532; a percentage of Ppeak 534; or a mean or median value of Rpeak 532, Ppeak 534, one or more percentages of Rpeak 532, one or more percentages of Ppeak 534 or any combination thereof.

Additionally or alternatively, the escape interval reset criteria may include a minimum RR interval requirement. The RR interval 562 from the current R-wave sensed event signal 554 to a previous sensed event is determined by cardiac signal analyzer 90 and compared to a reset interval 564. The reset interval 564 may be based on a tachyarrhythmia detection interval used in detecting a shockable rhythm. In one example, the reset interval 564 is equal to a VT/VF detection interval used by a shockable rhythm detection algorithm implemented in ICD 14, e.g., 300 ms in the example shown in FIG. 8. Other escape interval reset criteria, including a sensed event reset amplitude and/or reset interval, may be defined and based on a history of the patient's R-wave amplitude and/or RR intervals measured during sinus rhythm, during detection of a shockable rhythm, or during a post-shock sensing period 254 (shown in FIG. 5).

If reset criteria are satisfied, timing circuit 92 starts a hysteresis escape interval 528 in response to the R-wave sense event signal 554. In the example shown, if the peak amplitude of the sensed event is greater than the reset amplitude 560 or the RR interval ending with the currently sensed event is less than the reset interval 564, the escape interval is reset to the hysteresis escape interval, which is longer than pacing escape interval 524. Post-shock pacing is inhibited in response to large amplitude R-waves (greater than the reset amplitude), which may be evidence of a return of a normal intrinsic rhythm. Post-shock pacing is also inhibited in response to short RR intervals (less than the reset interval) that may indicate the presence of fine VF or other tachyarrhythmia during which pacing is undesirable. In examples including two ECG sensing channels 83 and 85, if the escape interval reset criteria are met by either one of the sensing channels 83 or 85, the currently running escape interval is reset to a hysteresis escape interval.

A post-sense decay sequence 552 is started by sensing module 86 in response to R-wave sense event signal 554 and a post-sense blanking interval 565. The R-wave sensing threshold 540 is automatically adjusted according to a post-sense decay sequence 552 until another pacing pulse is delivered or until the expiration of the post-shock sensing period 254 (FIG. 5). Upon each crossing of the R-wave sensing threshold 540 by filtered, rectified cardiac signal 501 outside post-sense blanking interval 565, R-wave sense event signals 556, 556' are 556" are produced by sensing module 86. Each of these sense event signals 556, 556' and 556" cause sensing module 86 to re-start the post-sense decay sequence 552, 552', 552" according to stored post-sense sensing control parameters. An initial threshold of the post-sense decay sequence 552 is based on the peak amplitude 558 of the most recently sensed event, which may be determined during the blanking interval 565 following R-wave sense event signal 554.

The post-sense decay sequences 552, 552', 552" may follow blanking interval 565 be controlled using the same sensing control parameters as the pre-shock decay sequence described in conjunction with FIG. 7. In one example, post-sense decay sequence 552 is controlled according to the same control parameters as the pre-shock decay sequence 405 with one exception. The initial amplitude, first decay rate, intermediate amplitude and second decay rate may all be set using the same sensing control parameters as during pre-shock decay sequence 405, but during the post-sense decay sequence 552 the post-sense drop time interval 566 is shorter than the pre-shock drop time interval 424. The post-sense drop time interval 566 does not expire in the example shown because an R-wave sense event signal 556 is produced during the drop time interval 566, causing sensing module 86 to restart the post-pace decay sequence 552'. Post-sense drop time interval 566 may be equal or unequal to post-pace drop time interval 522. In one example, the post-pace drop time interval 522 and the post-sense drop time interval 566 are equal, e.g., 700 ms, and less than half the pre-shock drop time interval 424, e.g., 1500 ms respectively.

In the example shown, each R-wave sense event signal 556, 556' and 556" corresponds to a sensed event that meets the escape interval reset criteria (each sensed event signal has a maximum peak amplitude that exceeds the reset amplitude 560). As such each R-wave sense event signal 556 causes the timing circuit 92 to reset the escape interval timer to the hysteresis escape interval 528' and 528". If the hysteresis escape interval 528, 528' or 528" expires before a sensed signal meets the escape interval reset criteria, a pacing pulse is delivered. In the example shown, each hysteresis escape interval 528, 528' and 528" is terminated upon receiving the respective R-wave sense event signals 556, 556' and 556" associated with a cardiac signal meeting the escape interval reset criteria. Other examples of sensed events that do not meet the escape interval reset criteria are described below in conjunction with FIG. 10.

In this way, timing circuit 92 controls the timing of post-shock pacing pulses to occur at the pacing escape interval 524 or the hysteresis escape interval 528 (terminated early in FIG. 8) during asystole or low-amplitude R-waves that are occurring at a rate that is slower than a VT/VF detection rate. Both high amplitude R-waves and short RR intervals cause post-shock pacing to be withheld by resetting the escape interval in response to either. As seen in FIG. 8, cardiac pacing pulses 504 and 514 are provided during a period of asystole (cardiac signal is flat-lined between pacing pulse deflections 502 and 512) until sensed intrinsic cardiac activity meeting escape interval reset criteria begins, in this case during the post-pace decay sequence 530'. If intrinsic cardiac activity does not meet the reset criteria during the post-shock pacing period 260, post-shock pacing will continue until the pacing period 260 expires. After the post-shock pacing period 260, cardiac signals are sensed according to the pre-shock sensing control parameters, and pacing therapy is delivered according to bradycardia, cardiac resynchronization therapy, anti-tachycardia therapy or other pacing therapy control parameters.

Figure 10:
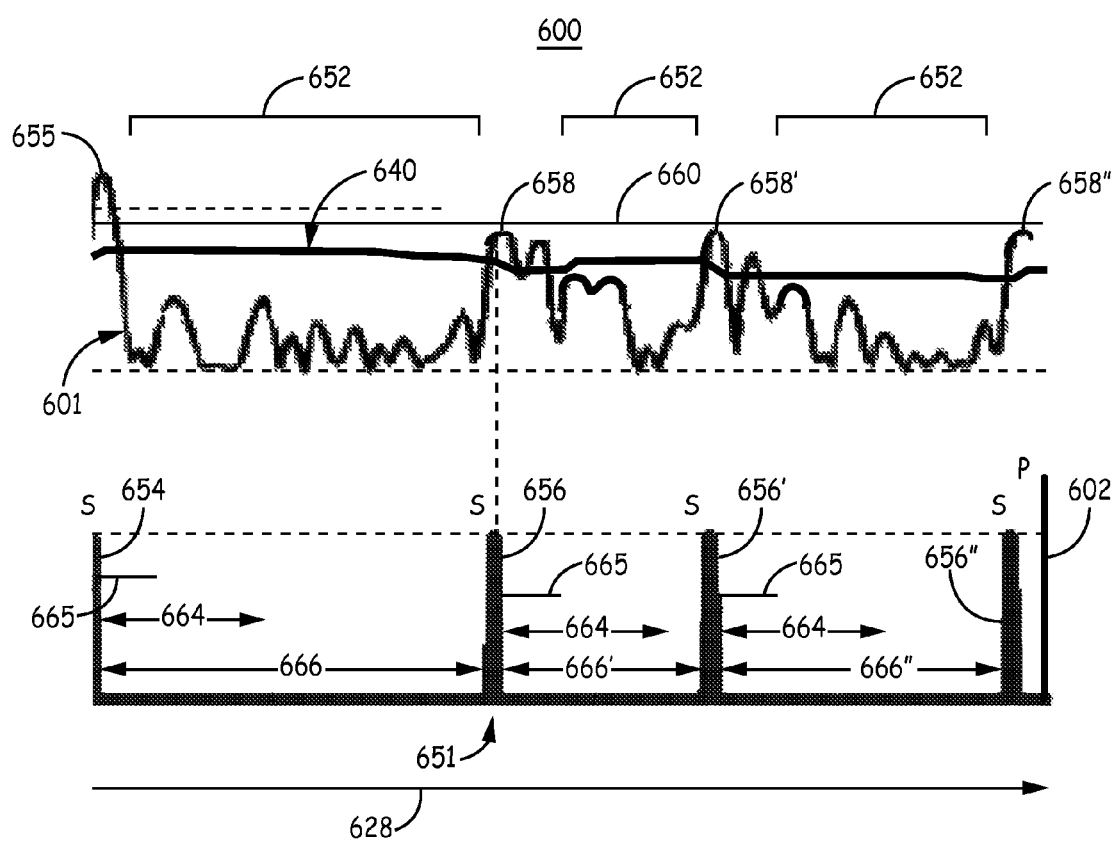
FIG. 10 is a timing diagram illustrating a cardiac electrical signal, an automatically adjusted R-wave sensing threshold and R-wave sense event signals produced by an ICD after according to another example.

FIG. 10 is a timing diagram 600 illustrating a filtered, rectified cardiac signal 601, automatically adjusted R-wave sensing threshold 640 and R-wave sense event signals 651. An R-wave sense event signal 654 is produced by sensing module 86 when the cardiac signal 601 crosses the R-wave sensing threshold 640 outside a blanking interval 665. Sensing module 86 restarts the post-sense decay sequence 652 (after blanking interval 665) according to sensing control parameters used during the post-shock sensing period 254.

Cardiac signal analyzer 90 determines the maximum peak amplitude 655 of the sensed cardiac event during blanking interval 665 and compares the maximum peak amplitude 655 to the reset amplitude 660. Since the maximum peak amplitude 655 exceeds the reset amplitude 660, timing circuit 92 resets the escape interval timer and starts a hysteresis escape interval 628 in response to the sense event signal 654. Cardiac signal analyzer 90 may additionally or alternatively determine the RR interval between the R-wave sense event signal 654 and an immediately preceding sense event signal. The RR interval is compared to a reset interval 664. If either the peak amplitude 655 is greater than the reset interval 660 or the RR interval is less than the reset interval 664, hysteresis escape interval 628 is started.

During hysteresis escape interval 628, the cardiac signal analyzer 90 receives three more R-wave sense event signals 656, 656' and 656" from sensing module 86 due to the cardiac signal 601 crossing the R-wave sensing threshold 640, outside blanking intervals 665, as it is automatically adjusted according to the post-sense decay sequence 652. In response to each R-wave sense event signal 656, 656', 656", cardiac signal analyzer 90 determines if the RR interval 666, 666' or 666" ending with the respective sense event signal 656, 656' or 656" is less than the reset interval 664 or if the sensed event peak amplitude 658, 658', 658" is greater than the reset amplitude 660.

In the example shown, the escape interval reset criteria are not met by the sensed events corresponding to any of the R-wave sense event signals 656, 656' and 656". As a result, the timing circuit 92 does not reset the escape interval timer, and hysteresis escape interval 628 continues running. When hysteresis escape interval 628 expires, the therapy delivery module 84 delivers a post-shock pacing pulse 602. As described above, a pacing escape interval (not shown in FIG. 10) is started by the timing circuit 92 in response to the pacing pulse 602, and sensing module 86 starts the post-pace decay sequence (not shown in FIG. 10) for controlling R-wave sensing threshold 640.

As shown in FIG. 10, an R-wave sense event signal 656, 656' and 656" produced by the sensing module 86 causes the post-sense decay sequence 652 to be restarted every time, but the timing circuit 92 does not reset the hysteresis escape interval 628 in response to every sense event signal 656, 656' and 656". Rather, resetting of the escape interval timer is based on analysis of the sensed events. Multiple R-wave sense event signals 656, 656' and 656" can occur during a hysteresis escape interval 628 (or during a pacing escape interval started in response to a post-shock pacing pulse), but unless the reset criteria are not met these sense event signals 656, 656', and 656" do not cause escape interval timer reset.

In addition to restarting a post-sense decay sequence 652, each sense event signal 656, 656' and 656" may be used, by tachyarrhythmia detector 94 for detecting a shockable rhythm according to an implemented detection algorithm. For example, the cardiac event intervals 666, 666' and 666" and/or morphology of the sensed signals may be compared to criteria for redetecting a shockable rhythm during the post-shock sensing period 254.

The cardiac signal 601 and R-wave sense event signals 651 are shown for one sensing channel in FIG. 10. As described above, two or more sensing channels may be used for determining when the escape interval timer is reset by timing circuit 92. In some examples, if cardiac signal analyzer 90 determines that a sensed event (outside a blanking interval) on either ECG channel 83 or 85 during the post-shock pacing period 260 is greater than the reset amplitude 660 or is sensed at an RR interval less than the reset interval 664, the hysteresis escape interval 628 is restarted. In other words, a sensed event on either sensing channel 83 or 85 that meets the reset criteria will cause timing circuit 92 to reset the escape interval timer.

Thus, a method and apparatus for controlling ICD functions after delivery of a CV/DF shock have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method performed by a medical device, comprising:
delivering an electrical shock to a heart of a patient;
setting an escape interval timer to start running an escape interval after delivering the electrical shock;
obtaining a cardiac electrical signal;
determining that the obtained cardiac electrical signal crosses a sensing threshold during the escape interval;
detecting a cardiac event within the cardiac electrical signal in response to determining the cardiac electrical signal obtained by the medical device crosses the sensing threshold during the escape interval;
determining if the detected cardiac event meets reset criteria, the reset criteria being different than the sensing threshold;
allowing the escape interval timer to continue running the escape interval if the detected cardiac event does not meet the reset criteria; and
resetting the escape interval timer if the detected cardiac event meets the reset criteria.

2. The method of claim 1, further comprising:
delivering a post-shock pacing pulse in response to the escape interval expiring;
restarting the escape interval timer to run a pacing escape interval in response to the post-shock pacing pulse; and
automatically adjusting a cardiac event sensing threshold according to a post-pace decay sequence controlled by a first set of sensing control parameters in response to the post-shock pacing pulse.

3. The method of claim 2, further comprising starting a post-sense decay sequence in response to sensing a cardiac event during the pacing escape interval, the post-sense decay sequence controlled by a second set of sensing control parameters different than the first set of sensing control parameters so that the post-pace decay sequence is different than the post-sense decay sequence.

4. The method of claim 3, further comprising:
setting a post-shock pacing period after delivering the electrical shock;
resuming a pre-shock decay sequence for automatically adjusting the cardiac event sensing threshold upon expiration of the post-shock pacing period, the pre-shock decay sequence comprising at least a drop time interval for controlling a decrease of the cardiac event sensing threshold from a starting threshold amplitude to an intermediate sensing threshold amplitude,
wherein the post-sense decay sequence comprises a post-sense drop time interval that is less than the pre-shock drop time interval.

5. The method of claim 4, further comprising:
setting a post-shock blanking interval during which cardiac event sensing by the medical device is disabled;
setting a post-shock signal analysis segment following the blanking interval during which cardiac event sensing by the medical device is enabled but pacing pulse delivery is disabled; and starting the post-shock pacing period upon expiration of the post-shock signal analysis segment, the pacing escape interval started during the post-shock pacing period.

6. The method of claim 2, further comprising:
determining a pre-shock cardiac event amplitude; and
setting an initial amplitude of the cardiac sensing threshold during the post-pace decay sequence based on the pre-shock cardiac event amplitude.

7. The method of claim 6, wherein determining the pre-shock cardiac event amplitude comprises producing a cardiac event template during a known pre-shock cardiac rhythm and determining a maximum peak cardiac event amplitude from the template.

8. The method of claim 2, further comprising:
determining a pre-shock R-wave amplitude;
determining a pre-shock P-wave amplitude; and
selecting an initial amplitude of the cardiac sensing threshold during the post-pace decay sequence based on an analysis of both of the pre-shock R-wave amplitude and the pre-shock P-wave amplitude.

9. The method of claim 1, wherein determining if the cardiac event meets the reset criteria comprises:
establishing a reset amplitude, the reset amplitude being larger than the sensing threshold;
comparing a peak amplitude of the sensed cardiac event to the reset amplitude; and
determining that the reset criteria are met if the peak amplitude exceeds the reset amplitude.

10. The method of claim 9, wherein establishing the reset amplitude comprises:
determining a pre-shock cardiac event amplitude; and
setting the reset amplitude based on the pre-shock cardiac event amplitude.

11. The method of claim 1, wherein determining if the cardiac event meets the reset criteria comprises:
establishing a reset interval;
determining a cardiac event interval from the sensed cardiac event to a preceding cardiac event;
comparing the cardiac event interval to the reset interval; and
determining that the reset criteria are met if the cardiac event interval is less than the reset interval.

12. The method of claim 11, wherein establishing the reset interval comprises setting the reset interval based on a tachyarrhythmia detection interval.

13. The method of claim 1, further comprising:
delivering a post-shock pacing pulse if the escape interval expires;
resetting the escape interval timer to a pacing escape interval in response to the post-shock pacing pulse;
wherein resetting the escape interval timer in response to the cardiac event meeting the reset criteria comprises setting the escape interval timer to a hysteresis interval that is longer than the pacing escape interval.

14. The method of claim 1, further comprising:
sensing a first plurality of cardiac events on a first cardiac electrical signal sensing channel of the medical device;
sensing a second plurality of cardiac events on a second cardiac electrical signal sensing channel of the medical device;
comparing each of the first plurality of cardiac events and each of the second plurality of cardiac events to the reset criteria;
resetting the escape interval timer each time one of the first plurality of cardiac events meets the reset criteria and each time one of the second plurality of cardiac events meets the reset criteria, wherein resetting the escape interval timer comprises resetting the escape interval timer to a hysteresis escape interval; and
delivering a post-shock pacing pulse if the hysteresis escape interval expires without at least one of the first plurality of cardiac events and the second plurality of cardiac events meeting the reset criteria during the hysteresis escape interval.

15. The method of claim 14, further comprising:
starting a post-sense decay sequence for automatically adjusting a first cardiac event sensing threshold of the first cardiac electrical signal sensing channel in response to every one of the first plurality of cardiac events; and
starting the post-sense decay sequence for automatically adjusting a second cardiac event sensing threshold of the second cardiac electrical signal sensing channel in response to every one of the second plurality of cardiac events.

16. The device of claim 1, wherein:
the therapy delivery module is configured to deliver a post-shock pacing pulse in response to the escape interval expiring;
the control module is further configured to reset the escape interval timer to a pacing escape interval in response to the post-shock pacing pulse,
wherein resetting the escape interval timer in response to the sensed cardiac event meeting the reset criteria comprises setting the escape interval timer to a hysteresis interval that is longer than the pacing escape interval.

17. A medical device, comprising:
a therapy delivery module configured to deliver an electrical shock to a patient's heart via electrodes coupled to the medical device;
a sensing module configured to receive a cardiac electrical signal, determine that the cardiac electrical signal crosses a sensing threshold, detect a cardiac event within the cardiac electrical signal in response to determining the cardiac electrical signal crosses the sensing threshold, and produce a cardiac event sense signal in response to detecting the cardiac event; and
a control module coupled to the sensing module and the therapy delivery module and configured to:
set an escape interval timer to start running an escape interval after the therapy delivery module delivers the electrical shock,
in response to receiving the cardiac event sense signal from the sensing module during the escape interval timer, determine if the detected cardiac event meets reset criteria,
allow the escape interval timer to continue running the escape interval if the detected cardiac event does not meet the reset criteria, and
reset the escape interval timer in response to the detected cardiac event meeting the reset criteria.

18. The device of claim 17, wherein:
the therapy delivery module is configured to deliver a post-shock pacing pulse in response to the escape interval expiring;
the control module is configured to restart the escape interval timer to run a pacing escape interval in response to the post-shock pacing pulse; and
the sensing module is configured to automatically adjust a cardiac event sensing threshold according to a post-pace decay sequence controlled by a first set of sensing control parameters in response to the post-shock pacing pulse.

19. The device of claim 18, wherein the sensing module is further configured to start a post-sense decay sequence in response to sensing a cardiac event during the pacing escape interval, the post-sense decay sequence controlled by a second set of sensing control parameters different than the first set of sensing control parameters so that the post-pace decay sequence is different than the post-sense decay sequence.

20. The device of claim 19, wherein:
the control module is further configured to set a post-shock pacing period after the electrical shock is delivered;
the sensing module is configured to resume a pre-shock decay sequence for automatically adjusting the cardiac event sensing threshold upon expiration of the post-shock pacing period, the pre-shock decay sequence comprising at least a drop time interval for controlling a decrease of the cardiac event sensing threshold from a starting threshold amplitude to an intermediate sensing threshold amplitude,
wherein the post-sense decay sequence comprises a post-sense drop time interval that is less than the pre-shock drop time interval.

21. The device of claim 20, wherein the control module is further configured to:
set a post-shock blanking interval during which cardiac event sensing by the sensing module is disabled;
set a post-shock signal analysis segment following the blanking interval during which cardiac event sensing by sensing module is enabled, but pacing pulse delivery by the therapy delivery module is disabled; and
start the post-shock pacing period upon expiration of the post-shock signal analysis segment, the pacing escape interval started during the post-shock pacing period.

22. The device of claim 18, wherein:
the control module is further configured to determine a pre-shock cardiac event amplitude; and
the sensing module is configured to set an initial amplitude of the cardiac sensing threshold during the post-pace decay sequence based on the pre-shock cardiac event amplitude.

23. The device of claim 22, wherein determining the pre-shock cardiac event amplitude comprises producing a cardiac event template during a known pre-shock cardiac rhythm and determining a maximum peak cardiac event amplitude from the template.

24. The device of claim 18, wherein the control module is further configured to:
determine a pre-shock R-wave amplitude;
determine a pre-shock P-wave amplitude; and
select a starting amplitude of the cardiac sensing threshold used by the sensing module during the post-pace decay sequence based on an analysis of both of the pre-shock R-wave amplitude and the pre-shock P-wave amplitude.

25. The device of claim 17, wherein the control module is further configured to determine if the cardiac event meets the reset criteria by at least:
establishing a reset amplitude, the reset amplitude being larger than the sensing threshold;
comparing a peak amplitude of the cardiac event to the reset amplitude; and
determining that the reset criteria are met if the peak amplitude exceeds the reset amplitude.

26. The device of claim 25, wherein the control module is configured to establish the reset amplitude by at least:
determining a pre-shock cardiac event amplitude; and
setting the reset amplitude based on the pre-shock cardiac event amplitude.

27. The device of claim 17, wherein the control module is configured to determine if the cardiac event meets the reset criteria by at least:
establishing a reset interval;
determining a cardiac event interval from the cardiac event to a preceding cardiac event;
comparing the cardiac event interval to the reset interval; and
determining that the reset criteria are met if the cardiac event interval is less than the reset interval.

28. The device of claim 27, wherein the control module is further configured to detect a tachyarrhythmia in response to the cardiac electrical signal by at least comparing cardiac event intervals to a tachyarrhythmia detection interval, the control module configured to establish the reset interval by setting the reset interval based on the tachyarrhythmia detection interval.

29. The device of claim 17, wherein:
the sensing module comprises:
a first cardiac electrical signal sensing channel configured to sense a first plurality of cardiac events;
a second cardiac electrical signal sensing channel configured to sense a second plurality of cardiac events;
the control module is configured to:
compare each of the first plurality of cardiac events and each of the second plurality of cardiac events to the reset criteria;
reset the escape interval timer each time one of the first plurality of cardiac events meets the reset criteria and each time one of the second plurality of cardiac events meets the reset criteria, wherein resetting the escape interval timer comprises resetting the escape interval timer to a hysteresis escape interval; and
the therapy delivery module is configured to:
deliver a post-shock pacing pulse if the hysteresis escape interval expires without at least one of the first plurality of cardiac events and the second plurality of cardiac events meeting the reset criteria during the hysteresis escape interval.

30. The device of claim 29, wherein the sensing module is further configured to:
start a post-sense decay sequence for automatically adjusting a first cardiac event sensing threshold of the first cardiac electrical signal sensing channel in response to every one of the first plurality of cardiac events; and
start the post-sense decay sequence for automatically adjusting a second cardiac event sensing threshold of the second cardiac electrical signal sensing channel in response to every one of the second plurality of cardiac events.

31. A non-transitory, computer-readable medium storing a set of instructions which, when executed by a control module of a medical device, cause the medical device to:
deliver a shock to a patient's heart via electrodes coupled to the medical device
set an escape interval timer to start running an escape interval after delivering the electrical shock;
obtain a cardiac electrical signal;
determine that the obtained cardiac electrical signal crosses a sensing threshold during the escape interval;

detect an R-wave within the obtained cardiac electrical signal in response to determining the cardiac electrical signal crosses the sensing threshold;
determine if the R-wave meets reset criteria; and
allow the escape interval timer to continue running the escape interval if the R-wave does not meet the reset criteria and reset the escape interval timer in response to the R-wave meeting the reset criteria.

* * * * *